US006193988B1

(12) United States Patent
Stoner, II et al.

(10) Patent No.: US 6,193,988 B1
(45) Date of Patent: *Feb. 27, 2001

(54) TUBER PLANTING SYSTEM COMPRISING CHITIN OR CHITOSAN

(76) Inventors: Richard J. Stoner, II, 432 W. Fifth Ave., Loveland, CO (US) 80537; Richard J. Stoner, Sr., 7258 Charring Ct. Cir. NW., Canton, OH (US) 44718; James C. Linden, 432 W. Fifth Ave., Loveland, CO (US) 80537; Kenneth W. Knutson, 1116 Morgan St., Fort Collins, CO (US) 80524; John H. Kreisher, 197 Farmingville Rd., Ridgefield, CT (US) 06877

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/680,320

(22) Filed: Jul. 12, 1996

Related U.S. Application Data

(62) Division of application No. PCT/US95/00401, filed on Jan. 12, 1995, which is a division of application No. 08/181,580, filed on Jan. 13, 1994, now abandoned.

(51) Int. Cl.[7] .......................... A01N 25/00; A01N 25/34; A01C 1/06
(52) U.S. Cl. ........................ 424/405; 424/408; 47/57.6; 504/100
(58) Field of Search ................. 435/410; 47/58, 47/57.6; 424/405, 408; 504/100

(56) References Cited

U.S. PATENT DOCUMENTS

| 2,651,883 | 9/1953 | Hedrick et al. . |
| 3,422,569 | 1/1969 | Lyon . |
| 3,441,528 | 4/1969 | Dede, Jr. . |
| 3,463,013 | 8/1969 | Reedy . |
| 3,545,129 | 12/1970 | Schreiber et al. . |
| 3,564,768 | 2/1971 | Hoffman . |
| 3,598,565 | 8/1971 | Graves . |
| 3,698,133 | 10/1972 | Schreiber . |
| 3,701,714 | 10/1972 | Okada et al. . |
| 3,707,807 | 1/1973 | Graves . |
| 3,862,007 | 1/1975 | Smirnoff . |
| 3,879,377 | 4/1975 | Austin . |
| 3,903,910 | 9/1975 | van Remmen . |
| 3,905,152 | 9/1975 | Loperfido . |
| 3,947,996 | 4/1976 | Watts . |
| 3,950,891 | 4/1976 | Hinkes . |
| 3,973,355 | 8/1976 | McKenzie . |
| 4,029,727 | 6/1977 | Austin et al. . |
| 4,067,141 | 1/1978 | Matsunaga et al. . |
| 4,068,602 | 1/1978 | Mickus . |
| 4,123,558 | 10/1978 | Poapst et al. . |
| 4,125,708 | 11/1978 | Masri et al. . |
| 4,149,340 | 4/1979 | DaVitoria-Lobo . |
| 4,160,342 | 7/1979 | Dryer . |
| 4,178,716 | 12/1979 | Harper et al. . |

(List continued on next page.)

FOREIGN PATENT DOCUMENTS

| 0-655-192-A2 | 5/1994 | (EP) . |
| 1574883 | 7/1969 | (FR) . |
| WO-8901288 | 2/1989 | (WO) . |
| WO-8907395 | 8/1989 | (WO) . |
| WO-8911795 | 12/1989 | (WO) . |
| WO-9118512 | 12/1991 | (WO) . |
| WO-9310095 | 5/1993 | (WO) . |
| 94/03062 | * 2/1994 | (WO) . |

OTHER PUBLICATIONS

"Chitosan as a Component of Pea–*Fusarium solani* Interactions," Lee A. Hadwiger, et al, Plant Physiology, vol. 66, 1980, pp. 205–211.*

"Chitin Oligosaccharides as Elicitors of Chitinase Activity in Melon Plants," Dominique Roby, et. al, Biochemical and Biophysical Research Communications, vol. 143, 1987, pp. 885–892.*

"Mechanical Signalling, Calcium and Plant Form," Anthony Trewavas and Marc Knight, Plant Molecular Biology, vol. 26, 1994, pp. 1329–1341.

"Oligosaccharins: Structures and Signal Transduction," Francois Cote and Michael G. Hahn, Plant Molecular Biology, vol. 26, 1994, pp. 1379–1411.

"The Salicylic Acid Signal in Plants," Daniel F. Klessig and Jocelyn Malamy, Plant Molecular Biology, vol. 26, 1994, pp. 1439–1458.

"Chitinase and Laminarinase Production in Liquid Culture by Trichoderma spp. and their Role in Biocontrol of Wood Decay Fungi," A. Bruce, et al., in *International Biodeterioration and Biodegradation*, 1995, pp. 337–353.

"Induction of Chitinases and β–1,3–glucanases in *Rhizoctonia solani*–Infected Rice Plants: Isolation of an Infection–related Chitinase cDNA Clone," Coimbatore S. Anuratha, et al., Physiologia Plantarum, vol. 97, 1996, pp. 39–46.

(List continued on next page.)

Primary Examiner—Sandra E. Saucier
(74) Attorney, Agent, or Firm—Santangelo Law Offices, P.C.

(57) ABSTRACT

A planting system involving a non-damaging stimulus (3) which is placed in the vicinity of a propagule (2) causes a naturally defensive substance (5) to be produced by the propagule. This substance may exist within an encapsulant (1) for a period of time so that the propagule may have enhanced disease control until it develops sufficiently to fend for itself. In one embodiment a large encapsulant surrounds a potato tuber. This encapsulant may include chitin to cause the release of chitinase through intermediate stimulants such as mRNA and activated carbon to absorb or release particular substances. The encapsulant is bound through the use of pentosan which acts with flaked chitin to achieve an outer casing and further protect the propagule both mechanically and chemically.

16 Claims, 5 Drawing Sheets

U.S. PATENT DOCUMENTS

| | | |
|---|---|---|
| 4,181,534 | 1/1980 | Headley . |
| 4,241,537 | 12/1980 | Wood . |
| 4,245,432 | 1/1981 | Dannelly . |
| 4,249,343 | 2/1981 | Dannelly . |
| 4,250,660 | 2/1981 | Kitamura et al. . |
| 4,286,087 | 8/1981 | Austin et al. . |
| 4,332,105 | 6/1982 | Nir . |
| 4,352,883 | 10/1982 | Lim . |
| 4,354,327 | 10/1982 | Smeltzer et al. . |
| 4,361,984 | 12/1982 | Dunstan et al. . |
| 4,368,591 | 1/1983 | Barke et al. . |
| 4,376,199 | 3/1983 | Koshugi . |
| 4,377,639 | 3/1983 | Lee . |
| 4,392,916 | 7/1983 | Nishiyama et al. . |
| 4,399,634 | 8/1983 | O'Hare . |
| 4,401,807 | 8/1983 | Koshugi . |
| 4,452,008 | 6/1984 | Sandhu et al. . |
| 4,473,648 | 9/1984 | Tang . |
| 4,489,205 | 12/1984 | Chu . |
| 4,532,156 | 7/1985 | Everest-Todd . |
| 4,562,663 | 1/1986 | Redenbaugh . |
| 4,569,914 | 2/1986 | Molnar et al. . |
| 4,575,519 | 3/1986 | Kifune et al. . |
| 4,586,288 | 5/1986 | Walton . |
| 4,612,725 | 9/1986 | Driver . |
| 4,670,037 | 6/1987 | Kistner, Sr. . |
| 4,672,035 | 6/1987 | Davidonis et al. . |
| 4,672,037 | 6/1987 | Daggett et al. . |
| 4,673,643 | 6/1987 | Schwengers . |
| 4,696,674 | 9/1987 | Cipar . |
| 4,699,135 | 10/1987 | Motosugi et al. . |
| 4,723,052 | 2/1988 | Cochran . |
| 4,753,035 | 6/1988 | Ryan et al. ............................ 47/57.6 |
| 4,804,750 | 2/1989 | Nishimura et al. . |
| 4,812,159 | 3/1989 | Freepons . |
| 4,813,176 | 3/1989 | Takayasu . |
| 4,833,238 | 5/1989 | DeLucca et al. . |
| 4,869,019 | 9/1989 | Ehrlich . |
| 4,892,825 | 1/1990 | Wumpelmann et al. . |
| 4,908,315 | 3/1990 | Kertz . |
| 4,910,146 | 3/1990 | Tur-Kapsa et al. . |
| 4,931,394 | 6/1990 | Krul . |
| 4,931,551 | 6/1990 | Albisetti et al. . |
| 4,932,404 | 6/1990 | Kifune et al. . |
| 4,940,840 | 7/1990 | Suslow et al. . |
| 4,957,866 | 9/1990 | Gupta et al. . |
| 4,960,703 | 10/1990 | Paques et al. . |
| 4,964,894 | 10/1990 | Freepons . |
| 4,978,505 | 12/1990 | Kertz . |
| 4,978,530 | 12/1990 | Strong . |
| 4,993,185 | 2/1991 | Adachi et al. . |
| 4,996,063 | 2/1991 | Inglett . |
| 4,996,792 | 3/1991 | Holtkamp, Sr. . |
| 5,021,207 | 6/1991 | DeLucca et al. . |
| 5,034,327 | 7/1991 | Takeyama et al. . |
| 5,041,290 | 8/1991 | Gindrat et al. . |
| 5,047,343 | 9/1991 | Joyce et al. . |
| 5,053,113 | 10/1991 | Krepets et al. . |
| 5,057,141 | 10/1991 | Kabana et al. . |
| 5,059,488 | 10/1991 | Detlefsen et al. . |
| 5,061,627 | 10/1991 | Olsen et al. . |
| 5,067,275 | 11/1991 | Constance . |
| 5,084,104 | 1/1992 | Heikkila et al. . |
| 5,087,475 | 2/1992 | Bazin et al. . |
| 5,089,272 | 2/1992 | Shioya et al. . |
| 5,089,401 | 2/1992 | Fujita et al. . |
| 5,089,607 | 2/1992 | Boni et al. . |
| 5,101,763 | 4/1992 | Creason et al. . |
| 5,106,640 | 4/1992 | Lehtomaki et al. . |
| 5,111,614 | 5/1992 | Holtkamp, Sr. . |
| 5,114,788 | 5/1992 | Nakagawa et al. . |
| 5,119,590 | 6/1992 | Izzard . |
| 5,127,185 | 7/1992 | Kojimoto et al. . |
| 5,127,187 | 7/1992 | Hattori et al. . |
| 5,129,180 | 7/1992 | Stewart . |
| 5,136,804 | 8/1992 | Rothem et al. . |
| 5,136,805 | 8/1992 | Mookherjee . |
| 5,136,807 | 8/1992 | Orlov . |
| 5,139,562 | 8/1992 | Vaughn et al. . |
| 5,168,059 | 12/1992 | Roberts . |
| 5,171,683 | 12/1992 | Kertz . |
| 5,173,419 | 12/1992 | Harman et al. . |
| 5,176,786 | 1/1993 | Debe . |
| 5,183,677 | 2/1993 | Lehtomaki et al. . |
| 5,185,253 | 2/1993 | Tumer . |
| 5,198,453 | 3/1993 | LaZonby et al. . |
| 5,374,627 | 12/1994 | Ito et al. ............................... 514/55 |
| 5,419,079 | 5/1995 | Wang et al. . |
| 5,554,445 | 9/1996 | Struszczyk et al. ................. 428/403 |
| 5,720,793 | 2/1998 | Kato et al. ............................... 71/16 |
| 5,733,851 | 3/1998 | Villanueva et al. ................. 504/292 |

OTHER PUBLICATIONS

"Hypersensitive and Enzyme Responses in Potato Tuber Tissue Treated with *Verticillium dahliae* and Arachidonic Acid," Steven F. Vaughn and Edward C. Lulai, vol. 69, 1992, pp. 105–116.

"Chemoperception of Microbial Signals in Plant Cells," Thomas Boller, Annual Review of Plant Physiology and Plant Molecular Biology, vol. 46, 1995, 189–214.

"A Method for the Quantitative Assessment of Wound–induced Chitinase Activity in Potato Tubers," M. Appel, et al., Journal of Phytopathology, vol. 143, 1995, pp. 525–529.

"Chitosanases—Properties and Applications: A Review," D. Somashekar and Richard Joseph, vol. 55, 1996, pp. 35–45.

"Pathogenesis–Related PR–1 Proteins are Antifungal," Thierry Niderman, et al., Plant Physiology, vol. 108, 1995, pp. 17–27.

"Temporal and Spatial Patterns of 1,3–β–glucanase and Chitanase Induction in Potato Leaves Infected by *Phytophthora infestans*," The Plant Journal, vol. 2, 1992, pp. 161–172.

"Chitosan Treatment: An Emerging Strategy for Enhancing Resistance of Greenhouse Tomato Plants to Infection by *Fuscarium oxysporum* f.sp. *radicis–lycopersici*," Pierre J. Lafontaine and Nicole Benhamou, Biocontrol Science and Technology, vol. 6, 111–124(1996).

"The Presence of a Thaumatin–like Protein, a Chitinase and a Glucanase Among the Pathogenesis–Related Proteins of Potato (*Solanum tuberosum*)," W.S. Pierpoint, et al., Physiological Molecular Plant Pathology, vol. 36, 1990, 325–338.

"Several 'Pathogenesis–related' Proteins in Potato are 1,3–β–glucanase and Chitinases," Erich Kombrink, et al., Proceedings of National Academy of Sciences, U.S.A., vol. 85, 1988, pp. 782–786.

"Pathogenesis–Related Proteins of Plants," Huub J.M. Linthorst, Critical Reviews in Plant Sciences, vol. 10, 1991, pp. 123–150.

"Difference Between Microbial Chitinase and Chitosanase in the Mode of Action on Partially N–acetylated chitosan," Mitisutomi, Masaru and Akira Ohtakara, in *Advances in Chitin and Chitosan*, ed. Charles Brine et al., Elsevier Applied Science, New York, 1992, pp. 304–313.

"Isolation and Characterization of the Genes Encoding Basic and Acidic Chitinase in *Arabidopsis thaliana*," Deborah Samac, et al., Plant Physiology, vol. 93, 1990, pp. 907–914.

Organic Chemistry, Norman L. Allinger, U of Georgia; Michael P. Cava, U of Pennsylvania; Don C. DeJongh, Wayne State U; Carl R. Johnson, Wayne State U; Norman A. Lebel, Wayne State U; Calvin L. Stevens, Wayne State U; Worth Publishers, Inc., 199, pp. 716–717 (1997).

"Transgenic Plants with Enhanced Resistance to the Fungal Pathogen Rhizoctonia solani", Karen Broglie. et. al., Science, vol. 254, Nov. 22, 1991, pp. 1194–1197.

"Specificity of Induced Systemic Resistance as Elicited by Ethephon and Tobacco Mosaic Virus in Tobacco", X.S. Ye, et. al., Plant Science, 84 (1992) pp. 1–9, Elsevier Scientific Publishers Ireland Ltd.

"Field Performance of Peat–lite Mix Encapsulated Small Minitubers", J.B. Melching, et. al., American Potato Journal, vol. 70, 1993, pp. 285–299.

"Cloned Chitinases in Fungal Plant–pathogen Control Strategies", Oppenheim, Amos B., and Iian Chet, Tibtech, Nov. 1992, vol. 10, pp. 392–394, Elsevier Science Publishers Ltd. (UK).

"Plant Membranes: A Biophysical Approach to Structure, Development and Senescence", Ya'acov Y. Leshem, Chapter 12, pp. 240–259 (1990).

"Field Performance of Small in vitro Derived Greenhouse–Produced Minitubers", J.B. Melching, et. al., The Potato Association of America, vol. 67, Aug. 1990, #8, p. 565 [abstract only].

"Alginate–Chitosan Coacervation in Production of Artificial Seeds", Ling–Fong Tay, et. al., Bitechnology and Bioengineering, vol. 42, pp. 449–454, 1993.

"Plant Signal Perception and Transduction: The Role of the Phosphoinositide System", Drobak, Bjorn K., Department of Cell Biology, John Innes Institute, John Innes Centre for Plant Science Research, Colney Lane, Norwich NR4 7UH, U.K(1991).

"Calcium Channels and Signal Transduction in Plant Cells", Eva Johannes, et. al., Bioessays, vol. 13, No. 7, Jul. 1991, pp. 331–335.

"Infectivity Titration of Corynebacterium sepedonicum on Russet Burbank and Centennial Russet Potatoes in Colorado", G.D. Franc, et. al., The Potato Association of America, vol. 64, 1987, p. 438 [abstract only].

"The Role of Contaminated Irrigation Water in the Recontamination of Erwinia–free Seed Potatoes", G.D. Franc, et. al., The Potato Association of America, vol. 64, 1987, p. 438, [abstract only].

"Day–Degree Model for Timing Early–blight Control in Colorado", G.D. Franc, et. al., The Potato Association of America, vol. 64, 1987, p. 438, [abstract only].

"A Novel Potato Seed Cutter Design and Its Efficacy for Reduction of Pathogen Spread During Seed Cutting", G.D. Franc, The Potato Association of America, vol. 69, p. 580, [abstract only](1990).

"Soft Rot Erwinia Bacteria in the Rhizospere of Weeds and Crop Plants in Colorado, United States and Scotland", N.J. McCarter–Zorner, et. al., Journal of Applied Bacteriology, 1985, 59, pp. 357–368.

"Presence of *Erwinia carotovora* in Surface Water in North America", M.D. Harrison, et. al., Journal of Applied Bacteriology, 1987, 62, pp. 565–570.

"A Simple Day–Degree Model for Initiating Chemical Control of Potato Early Blight in Colorado", G.D. Franc, et. al., Plant Disease, Oct. 1988, vol. 72 No. 10, pp. 851–854.

"Post Harvest Chemical Treatments for Control of Tuber Infection by *Alternaria solani*", M.D. Harrison, et. al., American Potato Journal, vol. 65, 1988, pp. 247–253.

"Evaluation of Sprinkler Application of Fungicides for Control of Potato Early Blight in Colorado", G.D. Franc, et. al., American Potato Journal, vol. 60, 1983, pp. 631–643.

Soft Rot Erwinia Bacteria in Surface and Underground Waters in Southern Scotland and in Colorado, United States, Nancy J. McCarter, et. al., Journal of Applied Bacteriology, 1984, 57, 95–105.

"Report of the International Conference on Potato Blackleg Disease", D.C. Graham, et. al., The Potato Association of America, 1985.

"The Dispersal of Phytopathogenic Bacteria", G.D. Franc, et. al., *The Movement and Dispersal of Agriculturally Important Biotic Agents*, Mackenzie, D.R., et. al., Editors, pp. 37–49, Claitor's Publishing Division, Inc., Baton Rouge, LA (1990).

"Colorado Rules and Regulations for Certification of Seed Potatoes", Colorado Certified Potato Growers Association, May 1992.

"Implications of New Technologies for Seed Potato Certification Programs and Seed Growers", K.W. Knutson, American Potato Journal, vol. 65, Apr. 1988, No. 4.

"Sugar Beet Crop At Risk", Janet Day, Denver Post, Nov. 12, 1993.

"World Potato Crop Facing Deadly Threat", Warren E. Leary, Denver Post, Oct. 31, 1993.

"Ethylene and the Regulation of Antifungal Hydrolases in Plants", Thomas Boller, Oxford Surveys of Plant Molecular & Cell Biology, vol. 5, 1988, pp. 145–174.

"Ethylene–regulated gene expression: Molecular cloning of the genes encoding an endochitinase from *Phaseolus vulgaris*," Karen E. Broglie, et. al, Proceedings of National Academy of Sciences, USA, vol. 83, Sep. 1986, pp. 6820–6824.

"Regulation of a Chitinase Gene Promoter by Ethylene and Elicitors in Bean Protoplasts," Dominique Roby, et. al, Plant Physiology, vol. 97, 1991, pp. 433–439.

Allen E., Phytopathologische Z. 69:151–9 (1970).

Nipoti et al., "Activity of Trichoderma haraianum rifai on the germination of asparagus seeds: I–Seed Treatments", Acta Horticulturae 271 : 403–406 (1990).*

Benhamou et al., "Induction of Systemic Resistance to Fusarium Crown and Root Rot in Tomato Plants by Seed Treatment with Chitosan", Phytopathology 84 (12) : 1432–44 (1994).*

* cited by examiner

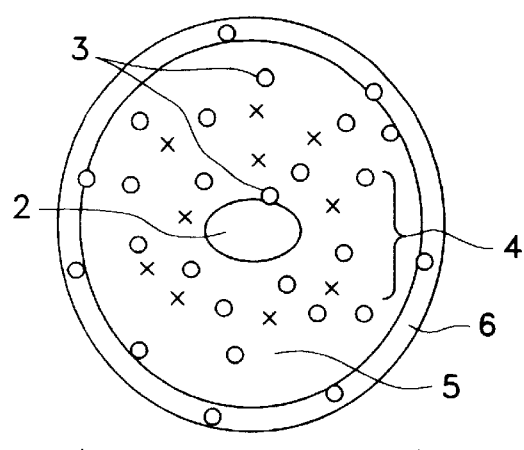
Fig. 1
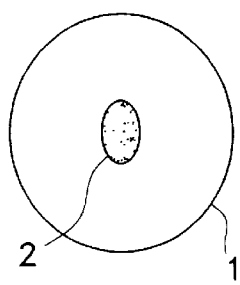 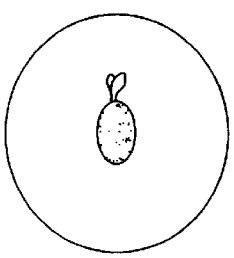 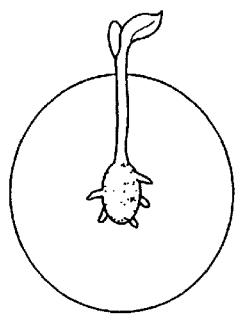 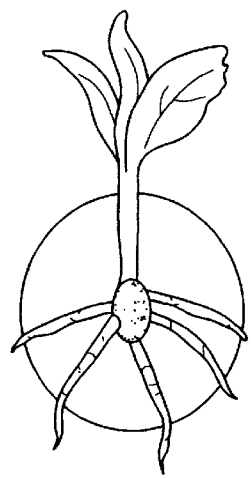
Fig. 2a    Fig. 2b    Fig. 2c    Fig. 2d
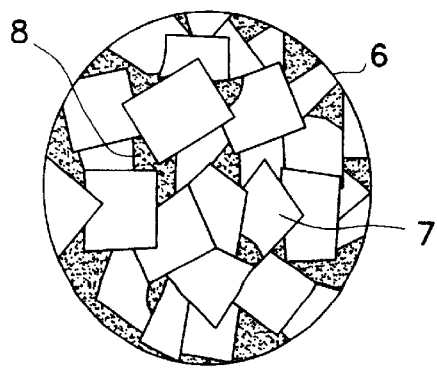
Fig. 3

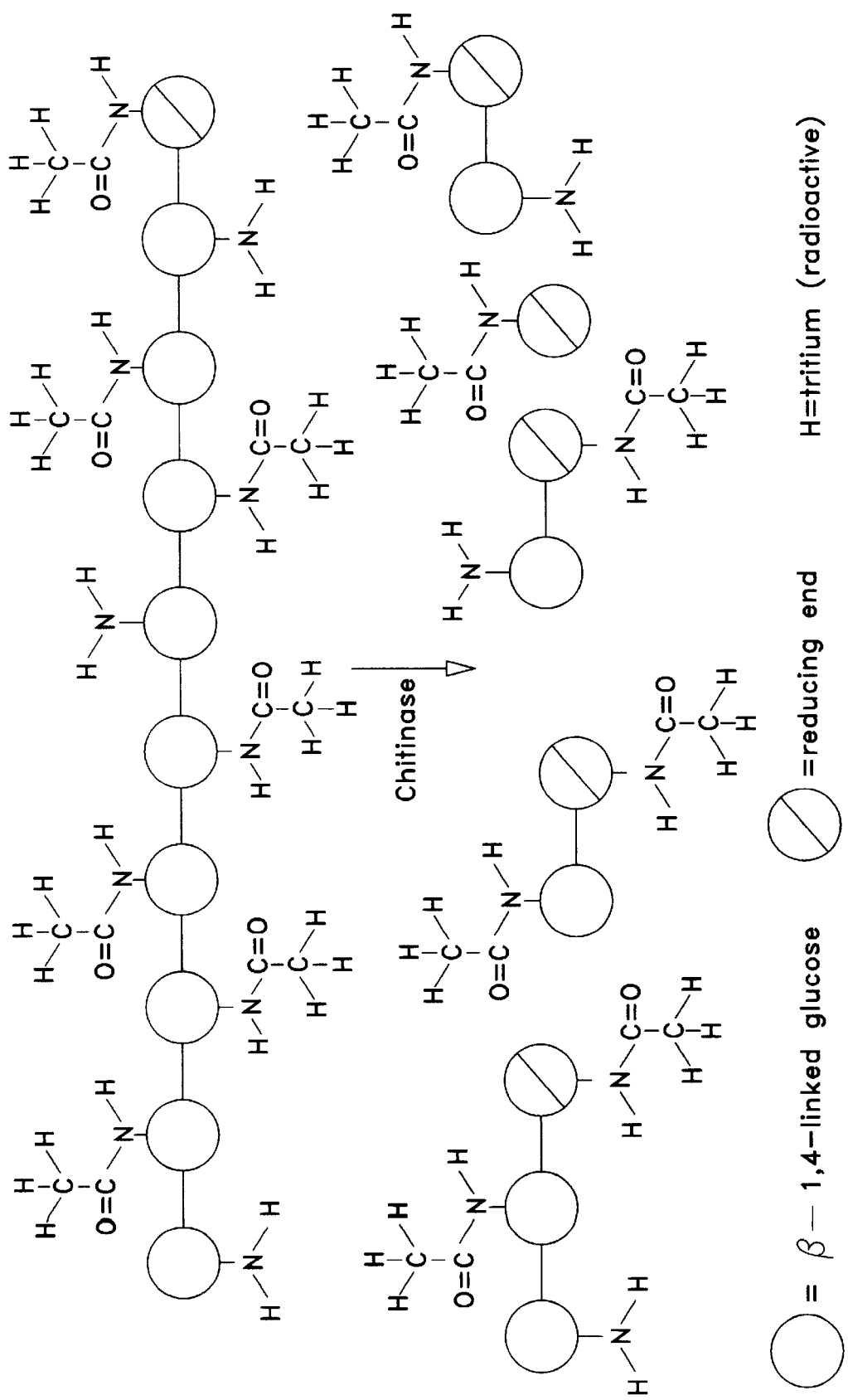
Fig. 4 Action of chitinase on radioactively labeled chitin.

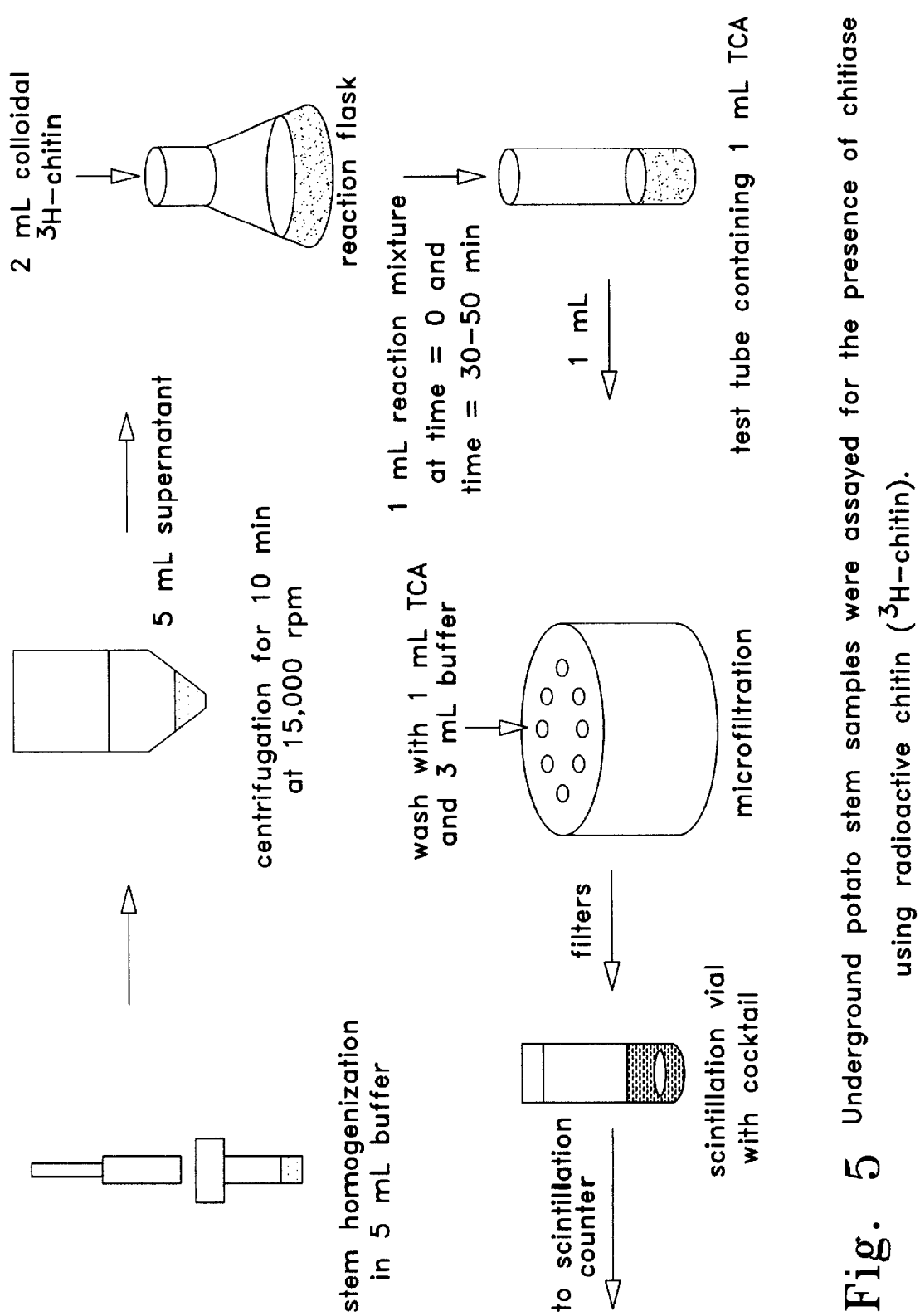
Fig. 5  Underground potato stem samples were assayed for the presence of chitiase using radioactive chitin ($^3$H-chitin).

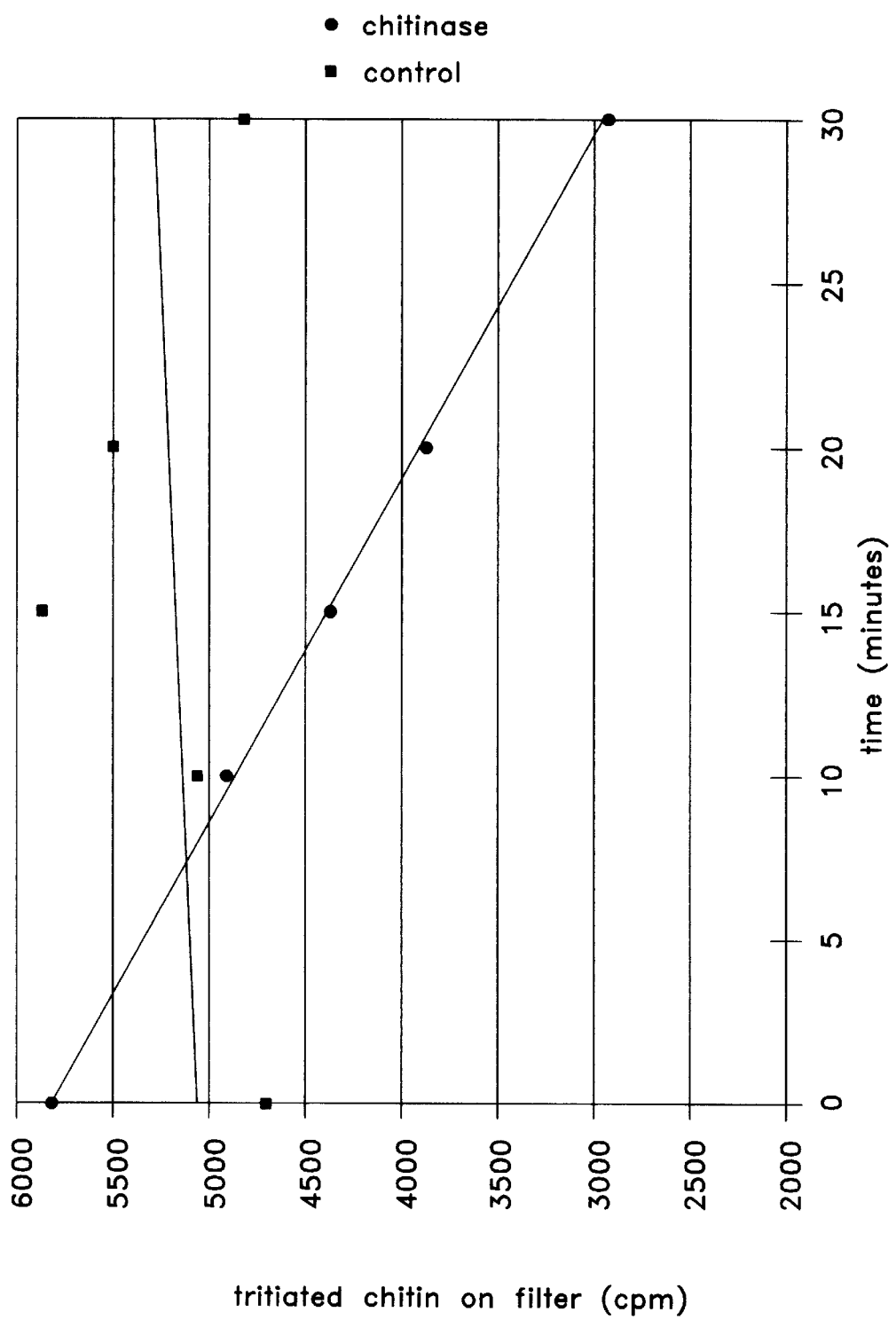

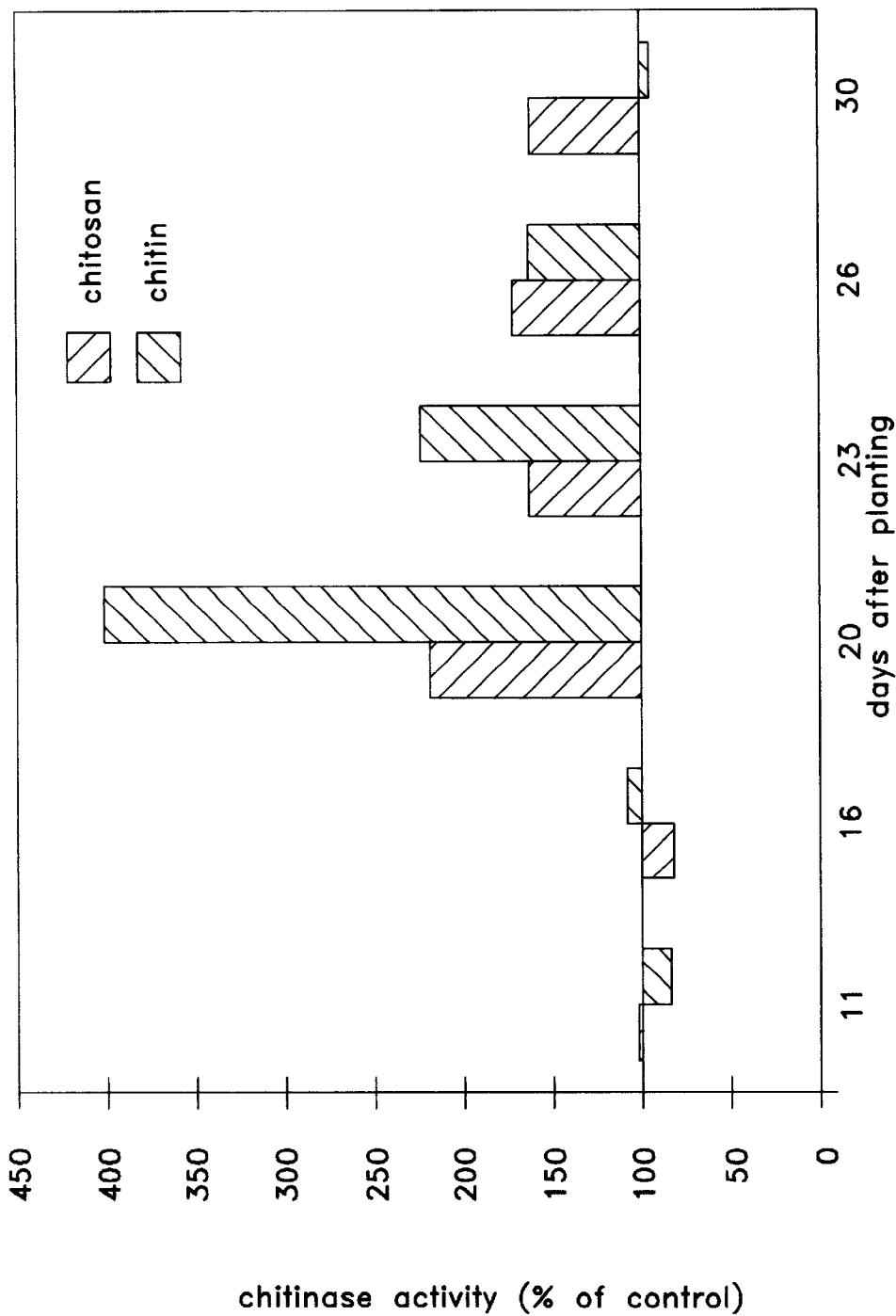
Fig. 7 Chitinase assays on underground stem material. Activity is calculated as drop in cpm per minute of reaction per gram fresh weight of stem. Decrease in cpm is difference between time = 0 and time = 30-50 minutes.

TUBER PLANTING SYSTEM COMPRISING CHITIN OR CHITOSAN

This is a divisional of Application No. PCT/US95/00401, filed Jan. 12, 1995, which is a divisional of U.S. application Ser. No. 08/181,580, filed Jan. 13, 1994, now abandoned.

I. TECHNICAL FIELD

Generally this invention relates to organic techniques for controlling disease in growing plants. Specifically the invention focuses upon techniques to organically control diseases which attack the potato plant under field conditions.

II. BACKGROUND ART

In any crop production endeavor, it has been desirable to produce not only high quantities, but also disease-free yields. These goals can be fairly easy to achieve or may be quite difficult depending upon the specific plant types involved. Often the farmer need only plant the beneficial specimens in a nurturing environment. The cultivars themselves then may develop relatively free from disease with little outside assistance. This can be especially true for cultivars or propagules which are reproduced through seed propagation. Most of the time the seed coating itself acts as a protective environment which allows the juvenile propagule not only to be stored relatively disease free, but also to begin its growth in a somewhat protected environment. The problem of disease control is, however, much more challenging for propagules which do not have the benefit of some shell-like protective coating. One group of propagules which do not have a shell-like coating is called tubers. Tubers include crop plants such as potatoes. Of this group, much attention has focused upon the problem of disease control for the potato.

The potato is unique in several regards. While it is a crop plant which has great commercial demand, it is also a tuber which is very vulnerable to fungus, bacteria, and viral diseases and often has a relatively short growing season. As it relates to the present invention, the potato's short growing season makes its early development very important to a successful crop. Although the present invention may be applied to a great variety of propagules, the potato's often extreme sensitivity highlights the benefit and function of the present invention.

As mentioned, the potato is very vulnerable to a variety of diseases. This is in part due to the fact that the potato is tuber propagated. Its sensitivity may be so extreme that at times entire crops have been impacted by the presence of only one disease in a specific area. Because these diseases can be spread very easily, the entire agricultural system with respect to potatoes has evolved somewhat uniquely. For instance an entire regulatory system has evolved in order to minimize the risks posed by diseases for this particular crop plant. As one example, the concern over introducing a disease to a crop may be so extreme that regulations have been enacted which make it literally illegal to import used farming equipment for use with the potato crop from one state to another. Additionally, the regulatory system at times limits the number of reproductions that a particular farmer may allow. This in essence mandates that every few years an entirely new, test-tube grown potato crop must be utilized by the farmer.

Even these extreme precautions often break down. When this happens if even one potato tuber is discovered to be infected by a disease, typically the entire crop must be destroyed and the crop residue rendered sterile. Some crops are even gamma ray irradiated to avoid the spread of that disease. Once this is accomplished the farmer must purchase certified seed tubers to begin a new growing cycle. While naturally the purchase of these certified seed tubers could be used every season, it is not economical to do so. Instead the potato farmer typically plants the offspring of that first season and continues that cycle for several years until, by regulation, they must start again with seed tubers which have been grown in essence in laboratory conditions and therefore are certified to be disease free.

As can be seen with respect to potato crops, the problem of disease control can be acute. In spite of these needs, there is also a need to minimize one's utilization of chemicals, chemically-formulated pesticides, chemically-formulated additives, and the like with respect to food production. It has become very desirable for any crop production intended for consumptive use to be able to be grown organically, that is without employment of chemically-formulated substances or at least to be grown in an environment which minimizes the utilization of unnatural effects such as the use of chemically-formulated pesticides (fungicides, insecticides and herbicides), genetically engineered changes, irradiation, and the like. While the desirability of a completely naturally grown product can rarely be debated, the actual implementation of these desires has, on a large scale, been very difficult to realize until the present invention. This has been especially true for very sensitive crops such as the potato. The present invention presents a system for organically controlling disease which may have particular applicability, but not be limited to, potato crops.

As mentioned, the desire for disease control has existed for years. Until the present invention two key techniques were prevalent for crops such as the potato crop. The regulatory approach mentioned earlier attempts to minimize the spread of undesirable diseases. This approach has met with only limited success. There still exist outbreaks of disease. Naturally, these vary in location and time; at present several concerns are bacteria ring rot and potato virus Y for the potato crop. Basically it simply has not been possible to completely eliminate the spread of disease through regulatory approaches. In addition, as markets have evolved, the demand for crops which are less likely to contain any disease has increased. Thus, while most regulatory approaches permit the utilization of a crop such as the potato to be reproduced for up to six growing seasons before its replacement with new, test-tube grown seed tubers, the consumers themselves have pushed for earlier crops such as those occurring in the third year.

The second approach to the problem of disease control has been very traditional—the use of pesticides. Often, this solution has not always been acceptable; consumers have expressed a desire for organically grown produce free of pesticides. In addition, the use of pesticides, although often fairly effective, has been accompanied by other problems. First, the pesticides need to be applied. This can be challenging in that broadcast application on a field basis may not provide the concentrated amount necessary at the particular plant. Second, to the extent the pesticide does not break down and remains in the soil, it may produce byproducts, or residual pesticide which can pose a problem of contamination. Thus pesticides can often result in unacceptable contamination of the remaining soils after the crop has been harvested.

The present invention takes an entirely different approach to the problem of the disease control. It presents a system which utilizes naturally occurring substances (like organic, substances which are not chemically-formulated) which are not harmful to the propagule and yet which trigger that propagule's own natural defense mechanisms. Thus, the propagule itself is prompted to provide a defensive substance in the vicinity of the propagule so that when a disease enters this vicinity, it is controlled even before the propagule may sense its presence. This is an entirely different approach from the main efforts in this field. By utilizing a known, naturally occurring trigger substance such as chitin, the invention acts in a manner to intensely trigger the plant's natural defensive mechanisms. Although the stimulating substances may have been known for years, by causing an intense stimulation the present invention is able to achieve an entirely different and unexpected result.

As mentioned, others may have utilized the particular substances involved. Even those inventions which utilize the chitin material have utilized it for vastly different purposes and had not applied it in the intense manner of the present invention. Their techniques have not been directed toward and have not achieved the unique results of the present invention. Rather they have sought completely different results. For instance, U.S. Pat. Nos. 4,812,159 and 4,964,894 to Freepons each sought to utilize chitosan (deacetylated chitin) to change the growth of specific plants. Contrary to the goals of the present invention, these references are aimed at altering a plant's natural growth and development; they also involve applying chitin at levels thousands of times less than the present invention. Similarly, the present invention takes an entirely different approach from that disclosed in U.S. Pat. No. 4,940,040 to Suslow in which genetically-altered bacteria were placed near a plant. The resultant man-made bacterial strains of Suslow take an entirely different direction from the organic approach of the present invention. Perhaps most illustrative of the vastly different directions taken by some is contained in U.S. Pat. No. 4,670,037 to Kistner. Somewhat like the Suslow reference, this reference involves intentionally placing a fungus near certain plants. Again it is directed away from the direction of the present invention as it is the separate organism, not the propagule, which accomplished the desired result. The Kistner reference also does not address the need for disease control; instead it might be characterized as tempting fate (let alone regulatory requirements) by purposefully placing a fungus near the a plant.

While there has unquestionably been a long-felt need to control diseases for potatoes, this need has not been completely satisfied even though the implementing substances and elements of the present invention had long been available. The inability of those skilled in the art to view the problem from the perspectives of the present inventors has, perhaps, been in part due to the fact that prior to the present invention those skilled in the art had not fully appreciated the nature of the problem. Rather than considering the possibility of an organic solution to the problem, the acute nature of the problem may have caused those skilled in the art to focus upon the pesticide approach mentioned earlier. They apparently had not fully appreciated that the problem of disease control could be achieved through organic means. While substantial attempts had been made by those skilled in the art to achieve disease control and to avoid the destruction of entire crops, the understanding which is the underpinning of the present invention and results it has been able achieve had not fully been understood.

Rather than taking the approach of utilizing a substance which stimulates the propagule's own natural defensive mechanisms, those skilled in the art actually taught away from this direction by utilizing an external substance which itself caused the disease control. Perhaps especially with respect to the present invention, the results achieved have been somewhat unexpected because those skilled in the art had utilized similar substances on similar propagules without the ability to achieve the results of the present invention. This has been attended by some degree of disbelief and incredulity on the part of those skilled in the art, however, by expanding the fundamental understanding of the mechanisms within the plant itself, the present invention may not only convince those skeptical of its approach, it may also cause further progress in this area.

III. DISCLOSURE OF THE INVENTION

The present invention discloses both the fundamental understandings and some specific arrangements which achieve a level of organic disease control for a propagule. The present invention also discloses arrangements which can achieve enhancement of emergence and yield for propagules. The present invention further discloses arrangements which increase the shelf-life of seeds by controlling germination and subsequent growth rate while still allowing the newly germinated plant to be planted by machine. The disclosed arrangement permits the goals of disease control, enhanced emergence and yield, and increased shelf-life by growth control to be achieved individually or in combination. In its preferred embodiment, the invention involves a system including an encapsulated propagule (such as a potato minituber). This encapsulant may include an intense stimulus, or elicitor, such as chitin. In addition, chitosan may also be used. While chitosan is not strictly an organic substance, it provides many of the advantages, albeit to different degrees, as chitin. The intense stimulus is not only non-damaging to the propagule, it also acts through various means to cause the propagule itself to release an amount of a naturally defensive substance (naturally defensive substance may, of course, include both substances which the propagule naturally is capable of releasing as well as those naturally defensive substances that may be produced as a result of genetic manipulations in which the gene(s) for such substances are introduced into a plant's genetic material). For crops such as the potato, this naturally defensive substance may be chitinase (chitinase is broadly defined to include the various forms of the family of chitinase enzymes that catalyze the depolymerization of chitin). The naturally defensive substance is released regardless of whether there is any disease present and is kept within the vicinity of the propagule so it is available when needed. Importantly, the naturally defensive substance is sufficient to disable or destroy the disease's ability to negatively impact the propagule. The invention also encompasses techniques for varying the system to accommodate a great variety of specific propagules, diseases, and needs. Once the disease is disabled, the system can automatically avoid impacting the propagule's growth. The propagule is allowed to naturally develop free from the effects of the disease. In this fashion, a very natural result is achieved. The system may thus assure an organically grown, naturally developed product.

Accordingly it is an object of the invention to achieve a natural and effective method for disease control for organized living cells. This includes propagules of those members of the plant kingdom which are of commercial interest (excluding fungi, bacteria, viruses and the like). Thus a goal is to avoid the use of chemicals such as pesticides, to avoid any genetic changes within the propagule itself, and to utilize the plant's own defensive capability in achieving disease control. In keeping with this general goal a more specific goal is to provide an insulated impact on the plant. Thus one goal is to allow an external stimulus to trigger the propagule's own processes and achieve disease control. Similarly another goal is to avoid any change in the natural growth development of the propagule. The present invention avoids any genetic changes and merely triggers the propagule's own natural processes. A further goal is to allow the plant to develop naturally and not have any changes except that of keeping the disease from negatively impacting the propagule's development. Thus a goal is to allow the plant to grow naturally without either a positive or a negative impact on its own developmental cycles.

Another broadly stated goal of the present invention is to provide a protection which lasts until the propagule is ready to do without that protection. In keeping with this goal the present invention affords an encapsulation which may exist over a several week period until that propagule has grown beyond a need for it. Naturally this is achieved while avoiding any utilization of potentially harmful substances.

Yet another general goal of the invention is to minimize the impact on the growing environment. Thus the invention concentrates its effects at the most important locations, near the propagule. This may reduce field application costs, and may avoid the residual impacts of using a broadly applied substance. In order to achieve this specific goal, it is a goal to avoid any application of the end disease control substance. Rather the goal is to utilize a naturally occurring intermediate substance which triggers the plant to achieve its own disease control.

An additional general goal of the invention is to utilize propagule encapsulation to enhance plant emergence and yield of plant product. Specifically, it is a goal to use propagule encapsulation to enhance emergence and yield separately or in addition to disease control and extended shelf-life as described below.

Another objective of the invention is to utilize propagule encapsulation to increase the shelf-life of seeds. In particular, a goal is to use seed encapsulation to restrict propagule growth such that the seed germinates but the resulting sprout does not extend beyond the encapsulant, thereby permitting the encapsulated propagule to be stored without refrigeration for extended periods and later to be planted by normal propagule-handling equipment. This contrasts with the normal situation in which seeds, once removed from refrigeration, germinate and subsequently must be planted without the use of equipment to avoid damaging the new sprout. Said differently, a goal is to develop a system which permits a propagule to age physiologically (i.e., the seed germinates and begins sprouting) while kept unrefrigerated, yet which enables the susceptible new propagule still to be planted with standard planting machinery. A further goal is to develop a system which can restrict propagule growth separately or in combination with disease control or enhancement of emergence and yield.

A further object of the invention is to take into account regulatory, unknown, and psychological factors which lead to broad commercial acceptance. Thus, the invention has as a goal the utilization of naturally occurring substances to cause the triggering of the effect within the tissue itself. This is achieved through an insulated approach whereby a stimulus acts through several different mechanisms before causing the existence of the naturally defensive substance. Thus, the placement of unnatural, potentially harmful, or otherwise unnecessary substances near the propagule is completely avoided. In keeping with this goal, it is an object of the invention to afford advantages to the farmer who is charged with actually implementing the system. By providing a system which can be uniformly sized and therefore achieve many of the goals of the farmer, the present invention is designed to be easily implemented and yet effective.

Naturally further objects of the invention are disclosed throughout other areas of the specification and claims.

IV. BRIEF DESCRIPTION OF DRAWINGS

FIG. 1 is a cross section view of an embodiment of the encapsulation according to the present invention.

FIGS. 2a–2d are sequential views of the developmental cycle of a potato plant according to the present invention.

FIG. 3 is an enlarged view of the encapsulation shown in FIG. 1 showing a tegumented outer casing construction.

FIG. 4 illustrates the action of chitinase on tritiated chitin.

FIG. 5 illustrates the chitinase assay procedure.

FIG. 6 illustrates the effect of chitinase on tritiated chitin.

FIG. 7 shows the levels of chitinase in underground potato stems over thirty days.

V. BEST MODE FOR CARRYING OUT THE INVENTION

As can be seen from the drawings, the basic concepts of the present invention may be embodied in many different ways. FIG. 1 shows a cross-section view of an encapsulated tuber. This represents a preferred embodiment of the present invention. As shown, encapsulant (1) may completely surround some propagule such as tuber (2). Encapsulant (1) may also include or be composed of a non-damaging stimulus (3). As discussed in detail later on, non-damaging stimulus (3) acts to organically control disease and thus achieve some of the goals of the present invention.

As shown in FIG. 1 it can be seen that non-damaging stimulus (3) may be provided in a vicinity of the propagule. This vicinity (4) may represent some spherical volume surrounding tuber (2) (as shown) or may merely be within some distance of the propagule. This distance should, however, be sufficiently close so that non-damaging stimulus (3) or its effects can, through some mechanism, be communicated to the propagule so as to affect it. Preferably, non-damaging stimulus (3) acts to provoke the propagule to release a natural defensive substance (5). Since the invention is fundamental in nature and thus encompasses a great variety of types or combinations of substances, naturally, the specific distances encompassed by the term "vicinity" includes a large variety. The term is functionally based to allow for a variety of situations through which non-damaging stimulus (3) might cause the desired affect on the propagule. For those substances which act at a large distance, the vicinity will accordingly be very large. Conversely, in instances where the particular substances chosen act only within a short distance, the vicinity will be appropriately smaller. Those skilled in the art could readily ascertain and compute or empirically determine when this function were present. Thus the term "vicinity" acts flexibly depending upon the particular mechanisms involved, the particular type of substances comprising the non-damaging stimulus, and the naturally defensive substance released by the particular propagule.

Importantly, particular combinations of substances contained by or comprising encapsulant (1) may be selected so as to allow the propagule to release naturally defensive substance (5). Thus, naturally defensive substance (5) is not fully confined and may travel in a relatively unimpeded fashion away from the propagule such as tuber (2). As shown in FIG. 1, naturally defensive substance (5) may be concentrated in the vicinity of tuber (2). As shown, naturally defensive substance (5) may travel in some fashion away from tuber (2) so that it may act at some distance from tuber (2). Again, the distance at which naturally defensive substance (5) acts may vary dependent upon the particular substances, diseases, propagules, and environments involved. It may also travel in primarily one direction (such as up) if that is the direction the particular disease tends to come from. This may be accomplished by proper shaping of encapsulant (1). For instance, an inverted cone shape may be utilized. As shown in FIG. 1, encapsulant (1) may not only completely envelope tuber (2) but it may substantially surround tuber (2). Thus, by encapsulating tuber (2) in a fashion which substantially surrounds tuber (2), tuber (2) is protected from all directions at some distance.

As also shown in FIG. 1, encapsulant (1) may include or have separately applied to it some type of outer casing (6). Outer casing (6) may act in a variety of ways. First, it may provide for a seal to further protect tuber (2) both mechanically and biologically. In the event outer casing (6) acts as a seal, it may be important to balance the degree to which outer casing (6) actually seals against the transfer of gases, liquids and the like. As those skilled in the art would readily appreciate, it may be important to allow some level of gas exchange between the outside environment through outer casing (6). It may also be appropriate to substantially seal tuber (2) against such effects. In instances in which outer casing (6) is actually some conditioned portion of encapsulant (1), the amount of sealing may be adjusted by the particular processes used in drying or curing encapsulant (1). Although this is discussed in more detail later with respect to the use of flaked chitin and the particular processes used to create encapsulant (1), it may be readily understood that by more rapidly or completely drying encapsulant (1) outer casing (6) may be formed in a more or less permeable manner. Again, the variation in outer casing (6) is broad as it may be adjusted as appropriate depending upon the needs of the particular propagule or the environment involved. By appropriately conditioning encapsulant (1) or separately applying outer casing (6) it may even be possible to achieve an inner environment of encapsulant (1) which is moist and conducive to plant growth while at the same time having an outer casing (6) which is relatively dry and further shields tuber (2) from undesirable impacts.

As mentioned earlier, encapsulant (1) may have a variable size and shape. Utilizing the particular substances and propagules of the preferred embodiment, it may be appropriate to size encapsulant (1) large. This may encompass the sizing of from ½" to 1½" in diameter when spherical encapsulation is utilized in conjunction with the particular propagule and substances of the preferred embodiment. Again, the term "large" encompasses a broad variety of sizes as it must necessarily be allowed to vary depending upon the particular type of propagule involved, the particular defensive mechanisms available, and even the particular substances and environments anticipated. As those skilled in the art could readily ascertain, the term is functionally based to allow for a variety of situations through which encapsulant (1) might assist in achieving one or more of the desired affects for the propagule. Specifically, it may be desirable that either encapsulant (1) be sized sufficiently large so that naturally defensive substance (5) might adequately protect the propagule or encapsulant (1) might be sized sufficiently large to allow the propagule to significantly develop before substantially exceeding the effects of encapsulant (1) and thus being exposed directly to the outside environment or encapsulant might be sized sufficiently large to accommodate easy planting by the farmer. Those skilled in the art could compute or empirically determine this aspect. As to when a propagule is considered to have substantially developed, this will vary based upon when the propagule is able to withstand disease on its own. With respect to the preferred embodiment involving a potato tuber as tuber (2), chitin as non-damaging stimulus (3), and chitinase as naturally defensive substance (5), it has been found that sizing of approximately 1" diameter for a spherical encapsulation meets the confines of the term "large." This particular size appears to be sufficient with respect to the current concern of diseases for the potato crop, specifically that of rhizoctonia. It also is sufficient to allow the potato tuber to adequately develop (about two weeks) before substantially breaking out of encapsulant (1). This age is sufficient to allow the potato's own natural defenses to develop so that by the time it breaks out of encapsulant (1) it is more readily able to overcome the effects of disease as may exist in the external environment. Again, this may vary based upon the particular diseases, propagules, and substances involved in any specific application.

In addition to actually locating non-damaging stimulus (3) in vicinity (4) of tuber (2), encapsulant (1) also serves to enable naturally defensive substance (5) to remain proximate to the propagule. Again, by the term "proximate", a variety of distances is intended once again depending upon the particular substances, plants, and environments involved. Functionally, it is important that a sufficient amount of naturally defensive substance (5) remain near the propagule so that disease is unable to substantially impact the propagule. Those skilled in the art could readily ascertain these limitations and could even compute or empirically determine when the necessary function is accomplished. The function of limiting substantial impacts upon the propagule may be accomplished by either acting at a distance from the propagule or by acting with sufficient intensity near the propagule so that the ultimate result—disease control—is achieved.

The distance within which naturally defensive substance (5) may remain proximate may be coextensive or may be a separate distance (larger or smaller) from that distance defining a vicinity within which non-damaging stimulus (3) is located. As shown in FIG. 1, non-damaging stimulus (3) is located throughout and within encapsulant (1). Naturally defensive substance (5) is also located within encapsulant (1), however, it is located in a smaller volume as shown. The particular substances selected for encapsulant (1) should enable naturally defensive substance (5) to be unaffected as to its ability to destroy or disable disease. It may also permit naturally defensive substance (5) to remain active near the propagule. This may be accomplished either biologically, mechanically, or chemically. Mechanically, encapsulant (1) may allow naturally defensive substance (5) to physically remain near the propagule. Chemically, it may avoid particular substances or include other substances which allow naturally defensive substance (5) to remain effective. For instance, since certain enzymes can break down certain naturally defensive substances; these enzymes may not be present within encapsulant (1) or proximate to the propagule to enhance the ability of naturally defensive substance (5) to continue to function.

Encapsulant (1) may contain a non-damaging stimulus (3) so that it may cause the propagule to release naturally defensive substance (5) substantially continuously. Unlike many chemical impacts upon a plant which are transient in nature, the present invention causes the plant to release a naturally defensive substance over a fairly long period of time. This release may be continuous so that the plant is constantly generating a larger and larger amount or additional amounts of naturally defensive substance (5). This not only allows the propagule to increasingly expand the area proximate to it within which disease is controlled, it also may allow it to prepare itself for exposure to the outside environment. Since it is anticipated that tuber (2) will be placed within encapsulant (1) in a disease-free environment, tuber (2) may begin to generate naturally defensive substance (5) even prior to its being planted. Thus, the tuber (2) may already have naturally defensive substance (5) proximate to it when it is exposed to diseases and other aspects through planting. Further, through the planting system of the present invention, the propagule will first be exposed to the potential of disease after it has already significantly developed the ability to control disease. Thus, storage and the like as a may be typically encountered may naturally enhance the desirability and abilities of the planting system according to the present invention.

The control of disease may be assayed through a variety of techniques such as those described with respect to Rhizoctonia in Horsfall, J. G. and Barratt, R. W., "Improved System for Measuring Plant Diseases," Phyto Pathology, 1945, vol. 35, p. 365, hereby incorporated by reference and through the use of other techniques which are well known in the art. For instance, with respect to Fusarium or Erwinia, simple procedures such as merely observing the propagule for decay are standard and effective assay techniques.

In one embodiment, the materials selected for encapsulant (1) may also be selected so as to allow encapsulant (1) to be somewhat flexible. Not only may some degree of flexibility allow encapsulant (1) to continue to surround tuber (2) even though subjected to mechanical shocks from handling and the like, but it may also allow encapsulant (1) to adapt somewhat as tuber (2) grows. For instance, as shown in FIGS. 2a–2d it can be seen that tuber (2) grows and eventually expands beyond the boundaries of encapsulant (1). As shown in FIG. 2b, to some extent encapsulant (1) may flex to accommodate the changing size and shape of tuber (2). The degree with which encapsulant (1) is considered flexible will of course vary based upon the substances and propagules involved. It is intended to encompass a functionally oriented aspect rather than one which is quantified. Further, encapsulant (1) may be made of some flexible substance or may be constructed so as to be flexible. The flexible substance may be contained throughout encapsulant (1) or only in outer casing (6). In the preferred embodiment this flexible substance may be both the flake-sized chitin which also serves as non-damaging stimulus (3) and the pentosan (8) or binder. Further, the construction technique may allow for flexibility. Again, through the use of flaked chitin, a tile-like or tegumented construction may be effected wherein each flake of chitin may move and shift and yet still maintain the appropriate sealing at outer casing (6). In keeping with the general goals of the invention by affording a flexible encapsulant, the present invention meets not only the disease control desires but also the ability to accommodate the needs of the farmer and allows for planter handling while avoiding damage to encapsulant (1). As the development shown in FIGS. 2a–2d demonstrates, in growing beyond the confines of encapsulant (1), the propagule is achieving completely natural growth. Growth is not altered, enhanced, or reduced by the effects of the chitin. Rather, the chitin merely acts to prevent disease from negatively impacting the propagule. This disease may be fungal as well as viral as it is possible that chitinase acts to kill certain viral concerns.

Through the construction described earlier, encapsulant (1) can reduce the need for field fertilization or preparation and can make it easier for the farmer to plant the propagule. By uniformly sizing encapsulant (1), the end result may actually allow for more automated planting and may thus reduce the labor and cost which most farmers face. Further, the design may accommodate the farmer's need to be able to store the propagules and may serve to maintain them in a storage environment with diminished concerns. Thus, by encapsulating tuber (2) prior to planting the farmer may receive a planting system which greatly simplifies his or her tasks. Naturally, it may also be possible to encapsulate the propagule at the time of planting.

Having discussed the overall invention in general terms, the specific preparation process may now be understood. While this process is discussed and has been developed with preparation on a small scale, it may naturally be adapted as appropriate to allow for large-scale production of encapsulated propagules. At present, however, only initial development techniques are most refined. Focusing upon the use of encapsulant (1) in conjunction with tuber (2) such as a potato tuber, small scale encapsulation has been successfully achieved. In reviewing the following process, it should be understood that the amounts utilized may be varied within keeping with the broad scope of the present invention. For small scale production, first about 16 grams of raw oats are selected and soaked in a sodium hydroxide solution for about two hours. The resulting oat substance is then repeatedly rinsed in 50 milliliters of water (distilled or not). This may be accomplished three times to yield an oats-based binding substance. This substance is then further soaked in 70 milliliters of some acid such as hydrochloric acid and again rinsed with 50 milliliters of water. This final rinsing may remove oligosaccharides and may appropriately establish the pH factor of the resulting substance. In this regard it should be noted that for potatoes a pH of approximately 4.6 to 5.5 seems appropriate. The resulting polysaccharide substance may then be mixed with one gram of clean, practical grade chitin. Since the chitin serves two purposes, namely, providing the non-damaging stimulus as discussed earlier as well as affording the tegumented construction also discussed earlier, it may be best to utilize practical grade, flaked chitin rather than chitin powder. To this combination 15 drops of some type of nutrient concentrate such as "Hydrosol" may be added along with two grams sucrose, and one gram of amino acids. Each of these serve as an appropriate fertilizer as those skilled in the art would readily understand. To the resulting substance ½ teaspoon of activated carbon may be added and again mixed with three grams of practical grade, flaked chitin. The final substance is then utilized to form the appropriately sized encapsulant around a disease-free potato minituber which is furnished for eventual planting. Once formed the resulting odorless encapsulated propagule may be dried above 34° in a humidity of less than 20% for about 36 hours. This results in an appropriate outer casing as discussed earlier. After dried, it has been found that the encapsulated minituber will store for weeks or months without negative effect. Further, once planted, encapsulant (1) not only acts flexibly but also causes the propagule to control disease in an enhanced fashion. Additionally, chitosan can be used instead of chitin to achieve a measure of disease control.

As a another embodiment, the materials selected for the encapsulant mix may include: pentosan (33 grams), calcium chloride and/or calcium nitrate (in an amount totaling 4 grams), fir and/or alder bark (20 to 80 mesh, in an amount totaling 100 grams), activated carbon (60 grams), humic acid (75 grams), Persolite (Persolite is a form of crushed volcanic rock and is manufactured by Persolite Products Incorporated) (200 grams), chitin or chitosan (30 grams of 80 mesh material), water (80 milliliters) and sufficient sodium hydroxide to adjust the pH to 5.9–6.0. If chitosan is used, it may be of the deacetylated or acetylated form. Deacetylated chitosan may have the added advantage of already including an amount (often about 17 percent) of chitin. Obviously, the preceding amounts can be scaled up according to the amount of material needed.

Another example of an encapsulating mixture is one which contains the materials just listed for the second embodiment, except that chitin is kept at about 3 percent or less of the total mix and chitosan is added in sufficient amount to total about 6 to 12 percent of the total mix by weight. Encapsulants prepared from such mixtures crumble or degrade particularly well once they become wet, and the encapsulant fragments do not reanneal once dry. Hence, this mix is particularly suited to cases in which the planter seeks enhanced emergence. However, this latter composition, as well as the others described herein, all have utility for encapsulations directed at achieving disease control, enhanced yield, enhanced emergence, or extended shelf-life.

Several sterilization techniques have been found to enhance emergence and yield beyond that achieved with encapsulation alone. One sterilization technique involves soaking seeds for two and one-half minutes to twenty minutes in a solution containing four parts water and one part five-percent sodium hypochlorite solution (e.g., Chlorox). Another sterilization method involves irradiating the encapsulant material with gamma rays prior to seed encapsulation.

As mentioned, encapsulant (1) may include not only non-damaging stimulus (3) but also other substances. As those skilled in the art would readily appreciate these other substances may enhance the overall planting system. One of the unique substances employed is that of activated carbon. The activated carbon serves a variety of functions. First, its nature allows air or other substance retention for ultimate release. In this regard it should be understood that the activated carbon or some other similar substance might be included within encapsulant (1) in an impregnated fashion so as to facilitate time-release or contact-based release of the particular substances when desired. Not only might the activated carbon release air to allow more complete sealing of outer casing (6), it may also release nutrients or even other chemicals should such be deemed desirable. This release may occur over time or only when tuber (2) begins to grow (germinate) and comes into contact with portions of encapsulant (1). Through this process oxygen molecules may be stored in the activated carbon to be released to activate primordia root development and inhibit growth of anaerobic potato pathogens. The activated carbon also controls ion bonding for phosphate, iron, and copper.

Additionally, the activated carbon may act as an absorbent itself to further minimize the migration of toxins, nitrates, contaminated ground water or other substances toward the propagule. Importantly, the activated carbon is a natural substance which does not leave any undesirable residue or materials in the field after the propagule has ultimately grown and been harvested. In protecting the propagule through their absorbent properties, both the carbon and the chitin (which is also absorbent) may act simultaneously to protect the propagule.

Encapsulant (1) may also contain other substances. While the nutrients are discussed to be primarily additives such as sucrose and the like, they may also encompass hormones, pesticides (fungicides, insecticides, herbicides, etc.) and other such substances. Admittedly, although pesticide usage is desired to be minimized through the present invention, the present invention does accommodate such usage in instances where it is necessary or desirable. Particularly is should be understood that it may not be possible to control all diseases or viruses through the organic means described in this invention. Thus combinations of effects may be desired. Further, encapsulant (1) might also include enzymes, acids, alkalines, and other fluids or substances as may be desirable for the specific propagule and environments involved.

A unique aspect of encapsulant (1) is that it utilizes a natural binding material. In the preferred embodiment the binding material may be derived from the oats and may be pentosan. The pentosan serves to flexibly hold the other substances of encapsulant (1). It also tends to break down when placed in the presence of water. Thus, when the propagule starts growing, the pentosan binder tends to yield more readily to the needs of the propagule. Further, through the process described earlier, the binder is not made so viscous as to inhibit natural development of the propagule; it's viscosity is believed to be less than a few thousand (ie. 4000) cps viscosity. Further, it is possible to include some type of spacing substance to hold the binder material away from the propagule since it may be water absorbent. Although in the preferred construction such a spacer is not necessary, if included it might be desirable that such a spacer not be a water absorbent so as to avoid drying out tuber (2).

Further, the binding material may also serve—either alone or in conjunction with other substances—as a medium through which other substances may be communicated to the propagule and through which yet other substances (particularly the naturally defensive substance) may be transported or communicated from the propagule. A unique aspect of such communications as envisioned for the preferred embodiment, is that these communications and the communication medium may be controlled or controllable, that is, both the timing and level of such communication may be affected externally. This is accomplished by utilizing a substance which when dry can close or reduce the pathway to communicate substances to or from the propagule and yet when moistened actually facilitates such communications. While a variety of materials may exhibit this property, in the present embodiment pentosan is utilized. Not only is pentosan a natural substance as discussed earlier, it also exhibits the property of being able to block or reduce osmotic or other communication when dry while yet remaining able to be re-moistened and thus re-open the communication pathways. Not only does its viscosity change as may be necessary to facilitate natural development of the propagule, the entire communication of stimulants, naturally defensive substances, and other substances may thus be controlled. This control may include establishing a level or time of communication and thus the level or time of the ensuing process or result. The degree of such communication may be adjusted by specifying the amount of drying (and, therefore, the amount of communication) when constructing the encapsulant or the amount of moistening after it has been constructed. For example, in applications where it is known that planting may occur within a relatively short time from encapsulation, the encapsulant and communication medium may not be completely dried to thus control the moisture content to coordinate the release with the anticipated planting time. Thus, the non-damaging stimulant may be fully communicated to the propagule even prior to planting so that it may build up some amount of the naturally defensive substance in advance of planting and exposure to disease and other harmful substances. Conversely, greater drying may be accomplished to harden an outer casing and not only enhance its protective effect but to also reduce the communication of the non-damaging stimulant to the propagule. The timing may be controlled by allowing the introduction of another substance such as water to open the communication pathway. Since the introduction of water may cause the growth process to commence (germination), this may conveniently coordinate the two events to occur simultaneously. The arrangement may serve to adjust the mechanical, chemical, and even biological level or timing of protection afforded the propagule. When exposed to water either through planting or intentionally to enhance disease control in advance of planting, the pentosan has reduced viscosity and may also activate the communication pathway. This may allow the stimulant, nutrients, or other substances to affect the propagule. Again for the preferred embodiment each of these may be controlled either at the point of manufacture or by the farmer prior to or upon planting as appropriate for the particular circumstances.

Referring to FIG. 3 it can be seen how an encapsulant according to the preferred structure may form outer casing (6). As shown, outer casing (6) involve a combination of flaked chitin (7) and pentosan (8). Flaked chitin (7) serves to form the tile-like or tegumented construction which assists in sealing encapsulant (1) from the environment at its exterior. Flaked chitin (7) may be held together by pentosan (8) at various locations. This may not only allow outer casing (6) of encapsulant (1) to flex and still maintain some type of seal but it also may act as a seal while still allowing some degree of gas exchange. Further, although the pentosan has been constructed of primarily of polysaccharides, it is believed that either poly- or oligo- saccharides may be utilized. Through the preferred construction, the oats-based binder may also be composed of or include glutaraldehyde. Regardless, when not dried out, the binder or some other substance in encapsulant (1) may serve as an osmotic pathway and thus act as some type of communication medium through which non-damaging stimulus (3) might affect the propagule. While in FIG. 1, the communication medium is shown as the material comprising encapsulant (1), it need not be. Further, this communication medium may also allow the unimpeded release of naturally defensive substance (5). This may occur through a variety of mechanisms but importantly, the communication medium should not substantially restrict the ability of the propagule to release naturally defensive substance (5).

In the preferred embodiment the non-damaging stimulus (3) which is provided in vicinity (4) is chitin. This particular substance has been selected because it yields the appropriate response for the particular potato propagule involved. Specifically chitin stimulates the release of a naturally defensive substance from a potato tuber. The chitin itself does not act upon the disease, rather, it causes the propagule to respond in such a fashion that the propagule itself controls the disease. Further, by using cleaned, flaked chitin encapsulant (1) can be constructed so as to achieve the tegumented exterior which assists in sealing tuber (2) from the environment. Additionally the chitin is intensely provided so that it sufficiently triggers the release of naturally defensive substance (5) in order to achieve the result of disease control. This is not just a difference of degree but rather the entire result and processes involved are different. While others have indicated that they might apply chitin to certain plants for different purposes, the amount of chitin or chitosan utilized for those applications is thousands of times less then that utilized by the present invention. The present invention utilizes approximately one-sixth of a gram of chitin per propagule. In contrast some others have applied chitin on the order of grams per acre. These are extraordinarily different levels. First, due to the short-lived nature of certain free enzymes, without intensely stimulating the propagule to release naturally defensive substance (5), disease control does not appear to be achieved. Second, by intensely stimulating the release, the propagule continuously releases naturally defensive substance (5) to develop a greater level of disease control then would exist naturally. While naturally defensive substance (5) might decay or lose its effectiveness over time, by intensely triggering its release the propagule may replenish this release or even expand the amount of substance in its proximity. Further, by providing the chitin intensely near the propagule the effect is concentrated at its most important point, namely, at the propagule. This differs dramatically from broadcast or other types of applications. While those types of field-based applications might still be utilized in keeping with the present invention, at present it is believed that an encapsulation technique works most effectively. Thus while there may be tens of thousands of propagules planted per acre, non-damaging stimulus (3) is provided in the vicinity of the propagule through an encapsulation technique. Again, the term "intensely" is functionally based as the specific mechanisms, substances, propagules, and environments may vary. While extraordinarily sensitive reactions may be discovered, as yet it appears that with the combination of chitin and the potato tuber the stimulation must be intense to the degree indicated in order to achieve the function of disease control. Again, those skilled in the art could readily ascertain when the function were present and could even compute or empirically determine when it were accomplished. The functionally based aspect for the preferred embodiment is that the non-damaging stimulus (3) be provided to a sufficient degree near or in vicinity (4) of the propagule so as to cause disease control.

Once provided, non-damaging stimulus (3) acts to cause the propagule to control certain diseases. This disease control may result in either killing the disease or in some fashion disabling it so that it may not affect the propagule. This control is further achieved from a natural substance which is emitted by the propagule's own processes. This natural substance thus acts defensively to protect the propagule from disease or other ill effects.

In keeping with the goal of providing an organic and natural disease control technique, natural processes are used to the largest extent possible. When a non-damaging stimulus such as chitin is placed near tuber (2), the chitin or some effect from it is communicated to the propagule. This may be accomplished either by the chitin actually touching the propagule or by some diffusion or sloughing process. Diffusion in the environment of a seed surrounded by a layer of encapsulating matrix, may involve a series of mass transfer processes between solid and liquid phases. Assuming the non-damaging stimulus is soluble in the liquid phase, the movement of that molecule from its point of origin in the encapsulating matrix to the surface of the plant is by means of a series of microscopic equilibria between the liquid phase and the solid particles of the matrix. Movement of the stimulant molecule depends on its relative solubility, the various attractions that might exist with the solid, and the concentration of the molecule at each phase. Higher concentrations of the stimulant in the encapsulating matrix will more aggressively drive the molecule toward the relatively lower concentration at the plant. Communication may also occur through some intermediate communication mode such as the non-damaging stimulus stimulating the release of yet another substance which then impacts the propagule. At present it is believed that the chitin sloughs off small portions to affect the propagule. These portions are communicated through the communication medium of encapsulant (1) to diffuse toward and ultimately touch the propagule. This process allows non-damaging stimulus (3) to affect the propagule.

Once the chitin touches the exterior of tuber (2), it is believed that the chitin impinges upon receptors in the plasmalemma which interact with a phosphoinositide signalling system. The oligosaccharides bind to receptors on the potato and induce enzyme production through a G-protein/inositoltriphosphate/calcium flux process called signal transduction. The signal transduction may also involve multiple phosphate-transfer reactions which begin with the autophosphorylation of the intracellular portion of membrane-associated receptors subsequent to the binding of a stimulant molecule. Thereafter, the receptor-bound phosphate may be moved by various kinases to a variety of other proteins as part of the transduction pathway. In the case of calcium transduction, however, molecules are formed which interact with the cytoplasm of the cell to cause the release of calcium from the cell's endoplasmic reticulum. This calcium is regarded as a secondary messenger or intermediate stimulant which may directly or indirectly interact with the cell nucleus to cause the release of messenger RNA. This mRNA may code for chitinase through a process involving particular enzymes. These enzymes (including protease inhibitors, phenylalanine lyase, chitinase, or β-1,3 glucanase) may then individually or in combination with other substances (e.g., hydrogen peroxide) or enzymes act to naturally defend the cell. Thus the mRNA is believed to act also as an intermediate stimulant to ultimately result in the release of enzymes such as chitinase from the cell. Through this process, the chitin acts to provoke the release of naturally defensive substance (5). Although the entire process is not fully understood and nay involve the combination of certain enzymes, through such basic understanding it is believed that it should be possible to vary the particular stimulus to suit the various diseases and plants.

Additional insight into the general mechanism can be gained by referring to the 1994 book edited by Klause Palme entitled "Signals and Signal Transduction Pathways in Plants" and the review by Thomas Boller, "Chemoperception of Microbial Signals in Plant Cells," Annual Review of Plant Physiology and Plant Molecular Biology, 1995, vol. 46, pp. 189–214, both of which are incorporated by reference.

The specific involvement of calcium and messenger RNA in the mechanism can be further understood by reference to: Johannes, E., et al., "Calcium Channels and Signal Transduction in Plant Cells," BioEssays, 1991, vol. 13, pp. 331–335; Trewavas, A. and Knight, M., "Mechanical signaling, calcium and plant form," Plant Molecular Biology, 1994, vol. 26, pp. 1329–1341; Schroder, M., et al., "Temporal and spatial patterns of β-1,3 glucanase and chitinase induction in potato leaves infected by *Phytophthora infestans,"* The Plant Journal, 1992, vol. 2, pp. 161–172; and Cote, F. and Hahn, M. G., "oligosaccharins: structures and signal transduction," Planta Molecular Biology, 1994, vol. 26, pp. 1379–1411, each of which are incorporated by reference. In addition, the actual methods for identifying various intermediates such as messenger RNA and calcium are well-known and readily found in the literature. As an example, a method for identifying messenger RNA is described in the article by Schroder, et. al, "Temporal and spatial patterns of β-1,3 glucanase and chitinase induction in potato leaves infected by *Phytophthora infestans*," The Plant Journal, 1992, vol. 2, especially pp. 161–172, and methods for monitoring intracellular calcium concentrations are discussed in the article by Johannes, E., et. al.,"Calcium Channels and Signal Transduction in Plant Cells," BioEssays, 1991, vol. 13, especially pp. 331–335, both of which are incorporated by reference as examples of the many various techniques which may be used.

Although the general process is somewhat akin to an immune reaction it is not entirely analogous to it. First, the chitin is a naturally occurring substance. Chitin occurs as exoskeletons of fungi, on insects and shellfish in great abundance. Second, the chitin is a non-damaging substance in that it is not an analog of the disease but rather merely something which causes the release of naturally defensive substance (5) which then may act upon the disease. The chitin will not likely be controversial nor will it have any propensity to cause disease on its own accord.

Although the preferred embodiment of this invention describes the use of chitin to trigger the synthesis of a naturally defensive substance such as chitinase, this invention is not limited to this example but includes other naturally defensive substances regardless of the release stimulant or mechanism such as chitosanase and the pathogenesis-related proteins (PR1; PR2; PR3; PR4; and PR5) that reduce disease symptoms associated with various fungal and bacteria infections as more fully described in Niderman, T., et al., "Pathogenesis-Related PR-1 Proteins are Antifungal," Plant Physiology, 1995, Vol. 108, pp. 17–27, and Hahlbrock, K. et al., "Several 'pathogenesis-related' proteins in potato are β-1,3 glucanase and chitinases," Proceedings of National Academy of Sciences, U.S.A., 1988, vol. 85, pp. 782–786, each of which is incorporated by reference. The pathogenesis-related proteins (the PR proteins) include the PR1 proteins (proteins that reduce disease symptoms of the fungi *Peronosporta tabacina, Phytophthora parasitica* and *Phytophthora infestans*), the PR2 proteins (β-1,3 glucanase enzymes that hydrolyze cell walls of some fungi), PR-3 proteins (proteins with chitinase and lysozyme activities that hydrolyze cell walls of bacteria and some fungi), PR4 proteins (proteins with demonstrated anti-fungal activity) and the PR5 proteins (thaumatin-like proteins that have demonstrated anti-fungal activity).

Apart from merely controlling disease, the invention has ability in potentially shortening the reaction time of the plant to an existence of disease. A plant's natural reaction to disease may involve a somewhat slower process such as the hydrogen peroxide—lipid oxidation—phenylalanine lyase—hydrolytic enzyme process or other such processes as discussed in Thomas Boller, "Chemoperception of Microbial Signals in Plant Cells," Annual Review of Plant Physiology and Plant Molecular Biology, 1995, vol. 46, pp. 189–214 and in Linthorst, H. J. M., "Pathogenesis-Related Proteins of Plants, Critical Reviews in Plant Sciences, 1991, vol. 10, pp. 123–150. The present invention may serve to bypass some of this or similar processes and result in a more direct release of the naturally defensive substance. This more direct release process may occur in a fraction of a time it takes for the usual response. Since the usual response can take on the order of several days, the invention's shortening of this time can have significant effects on the resultant healthy development of the plant. The plant may thus accelerate its elimination of disease or its wound healing capabilities. Further, this type of accelerated enzyme production does not inhibit regular plant development. Application of the invention to focus on this aspect may naturally be varied from a strict encapsulation mode to other more topical modes.

Additionally the mechanisms described are selected to further insulate the propagule from outside effects. By not directly triggering the release of naturally defensive substance (5), the non-damaging stimulus is less likely to be undesirable. Rather, an intermediate stimulus such as the calcium or the messenger RNA may be involved. This might occur either within the cell or external to the cell as may be readily appreciated. In keeping with the concept of insulating the propagule from specific effects it can be seen that the present process involves an intermediate stimulus within the cell and then a second stimulant from the cell nucleus itself. Each of these may be caused to exist within the cell's cytoplasm without damaging the cell wall. This specific process may also involve an intermediate stimulant which is a material from the cell nucleus, namely, messenger RNA. This again further insulates the process from being considered artificial and makes it less likely that unintended effects or results are involved. Ultimately the chitinase is released as a naturally defensive substance (5) and is caused to exist proximate to the propagule for some period of time. With respect to potato tubers this may be several weeks after growth has begun so that the potato tuber may adequately develop its defense mechanisms. As shown in FIG. 2c at some point the potato tuber will break out of encapsulant (1) however, the propagule may still be affected by the non-damaging stimulus. Thus the plant may still be caused to release its naturally defensive substance throughout—even remote from the encapsulated material. At some point the propagule should have sufficient abilities to fend for itself without enhanced protection.

As may be easily inferred from the test data shown in Table 1 and Table 2, this invention has applicability to a variety of plants and naturally defensive substances. The test data in Table 1 and Table 2 demonstrate the use of non-damaging stimuli to achieve a reduction in the incidence of disease, as well as enhanced yield and emergence. Further, by selecting appropriate stimulants which trigger similar plant mechanisms and appropriate propagules with similar physiological characteristics one could predict stimulants and plants which would achieve similar results with a relatively high degree of success.

While the chitin/chitinase process seems to work well with respect to diseases currently of concern for the potato crop, it should be noted that chitinase may not work for every disease. Chitin-producing fungi are also affected by chitinase. Naturally the particular substances may be varied and yet still fall within the scope of the present patent. For instance, there has been some suggestion that β-1,3 glucanase might alone or in combination with other substances (such as chitinase) cause the destruction of blue mold. Similarly, it may be possible to utilize protease inhibitors, phenylalanine lyase, chitinase, or β-1,3 glucanase to achieve the desired end results. Further the propagule might also be varied as well as the process to produce the naturally defensive substance. For instance, it appears that the following plants are capable of producing chitinase as one possible naturally defensive substance:

Papaya latex, Fig latex, Turnip root, Wheat germ, Tomato Stem, Bean leaf, Hevea latex, Yam tuber, Soybean seed, Rubus cell, Tobacco leaf, Parthenocissus cell, Carrot cell, Melon plant, Cucumber leaf, Barley seed, Pea pod, Potato leaf In fact, it is expected that knowledge of whether a plant naturally expresses the chitinase gene will prove to be a valuable tool in selecting which plants will most benefit from the chitin or chitosan process described in this invention. For example, the encapsulation mixture containing chitin or chitosan is believed to trigger the chitinase gene in bean plants (as shown above, a plant thought to have the chitinase gene) and thus achieve a level of disease control. Naturally, other such plants may be discovered. An organic disease control system according to the present invention might be implemented for each as well as other plants which produce other naturally defensive substances. It may also be possible that certain combinations might be utilized to achieve disease control for more than one disease. Again, in keeping with the broad disclosure of the present invention and the scope of the patent granted to it, each of these variations would fall within the scope of protection for the present invention.

Based upon an understanding of the fundamental characteristics of the disclosed non-damaging stimuli, identification of other non-damaging stimuli is possible. For instance, one might first identify various substances that do not appear to cause any damage to a propagule. Such substances might next be tested to determine if that substance is one which is known to cause the release of a naturally defensive substance through any mechanism. As mentioned earlier, this mechanism might be direct or might be accomplished through a variety of intermediate steps such as the release of calcium, messenger RNA or the like. With this information, it would be straightforward to identify non-damaging stimuli which cause the release of a naturally defensive substance, regardless of the multitude of substances, propagules, and mechanisms available. This might be accomplished empirically or by mere literature searching.

While the foregoing discussion has centered on the use of naturally defensive substances such as chitin or chitosan to protect plants from disease, emergence results listed in Table 4 for tests in which chitin or chitosan were added to encapsulation mixtures demonstrate that the presence of chitin or chitosan can be used to enhance emergence of potato propagules as well. It should also be possible to use chitin and chitosan in combination to achieve similar results. The ability to enhance emergence and yield can be achieved independently or in combination with disease control, enhanced yield, or the ability to extend shelf-life.

Furthermore, as can be seen in Table 4, it has been possible to use the described encapsulation mixtures to increase the amount of time at which the seeds can be stored at room temperature and restrict the extent to which the seed grows after germination (i.e., to increase shelf-life). Hence, encapsulation has the further advantage of allowing propagules to age physiologically (i.e., begin sprouting), while still enabling the newly growing propagule to be planted with standard propagule-planting machines rather than resorting to traditional hand-planting to avoid damaging the newly sprouted propagule. This benefit can be achieved independently or in combination with disease control, enhancement of emergence, or enhancement of yield.

Additionally, as shown in Table 3, encapsulation utilizing a naturally defensive substance such as chitosan has been demonstrated to enhance yield. Here too, the benefit of encapsulation, in this case enhanced yield, can be achieved individually or in combination with disease control, enhanced emergence, or the ability to extend shelf-life.

Procedures and test results demonstrating that encapsulation with chitin actually stimulates the production of chitinase are contained in Table 5.

The foregoing discussion and the claims which follow describe the preferred embodiments of the present invention. Particularly with respect to the claims, it should be understood that changes may be made without departing from its essence. In this regard, it is intended that such changes would still fall within the scope of the present invention. It simply is not practical to describe and claim all possible revisions to the present invention which may be accomplished. To the extent such revisions utilize the essence of the present invention, each would naturally fall within the breadth of protection encompassed by this patent. This is particularly true for the present invention since its basic concepts and understandings are fundamental in nature and can be broadly applied.

Any references mentioned in the application for this patent as well as all references listed in any information disclosure and the Tables filed with the application are hereby incorporated by reference in their entirety to the extent such may be deemed essential to support the enablement of the invention(s), however, to the extent statements might be considered inconsistent with the patenting of this/these invention(s) such statements are expressly not to be considered as made by the applicant(s).

The Rhizoctonia test data reported in Table I were conducted by Southern Idaho Agricultural Researchers and Consultants, an independent testing station. The tests monitored the occurrence of stem cankering caused by Rhizoctonia on certified greenhouse-grown Russet Burbank minitubers encapsulated with 960 milligrams of chitin per as compared to unencapsulated minitubers without chitin. The results demonstrate a statistically significant reduction in stem cankering for the plants encapsulated with chitin.

The Fusarium and Erwinia test data were conducted by an independent laboratory at Michigan State University. Test results were as described for Rhizoctonia, except that seed piece decay resulting from Fusarium or Erwinia was monitored. Again, statistical reduction in the incidence of disease was observed relative to controls.

TABLE 1

Chitin encapsulation of potatoes as method of disease control.

| Treatments | Pathogen: | |
|---|---|---|
| | Fusarium/ Erwinia Seed Piece Decay Mean | Rhizoctonia % of Stem Cankering Mean |
| Control Minitubers R. Burbank | 1.0a | 3.07a |
| 0.96 grams chitin per encapsulated Minitubers R. Burbank | 0.4b | 0.39b |

P = 0.01

TABLE 2

Chitin and Chitosan encapsulation of cut seed potatoes as a method of disease control of Rhizoctonia.

| Treatments: | Control - cut seed piece alone | 0.60 grams chitin per encapsulated cut seed piece | 0.60 grams chitosan per encapsulated cut seed piece |
|---|---|---|---|
| Mean | 4.51 a | 3.21 b | 3.30 b |

P = 0.05

Table 2 lists results with Russet Ranter potatoes grown in a chitin or chitosan encapsulation matrix that demonstrate resistance to Rhizoctonia. The eyes of the field grown Russet Ranger seed potatoes were removed with a melon ball scoop and allowed to suberize for 72 hours. They were then encapsulated with 0.60 grams of chitin or chitosan per seed piece and then planted in a random block test plot. After emergence, the potato plants were inspected for Rhizoctonia stem cankering. Table 2 shows that chitin or chitosan encapsulation treatments caused a statistically significant reduction of Rhizoctonia cankering.

TABLE 3

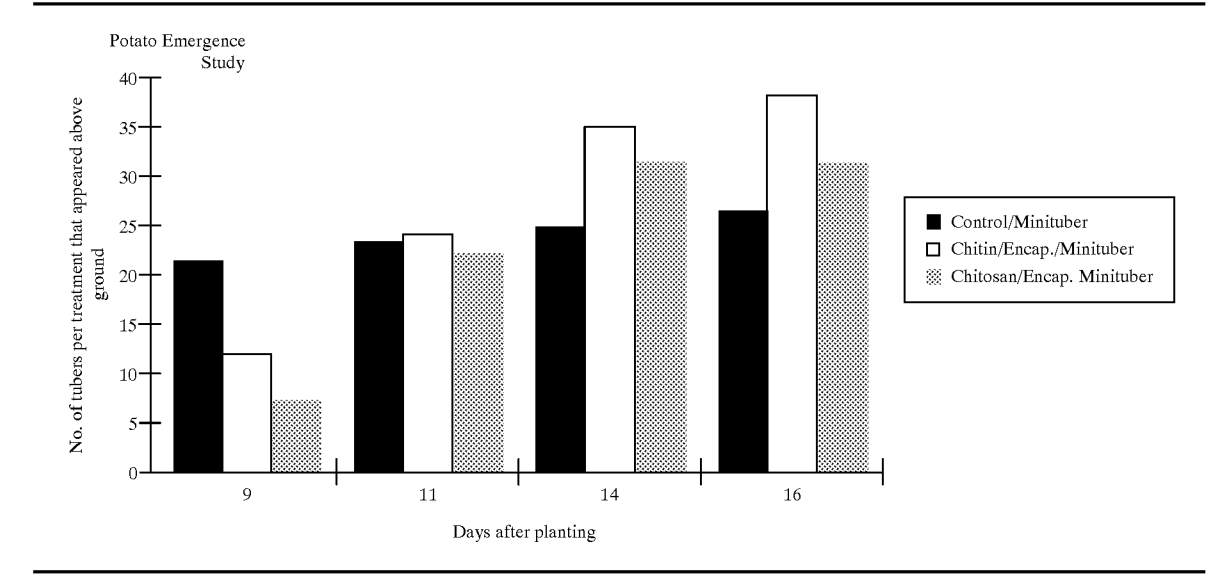

The above figure shows emergence data obtained during a greenhouse study with encapsulated minitubers as compared to those encapsulated with chitin or chitosan. The test involved planting 40 minitubers each of unencapsulated minitubers and those encapsulated with 0.96 grams of chitin or chitosan. As demonstrated in the above figure, the emergence rate of seedlings from encapsulated minitubers was superior compared to unencapsulated minitubers. In particular, although more of the control tubers than encapsulated tubers appeared at the soil surface at day 2, emergence rates for all treatments were the same on day 11 and the rate for controls fell behind those of the encapsulated tubers (for which 95 percent germination was noted) by day 14.

TABLE 3

Yield data on Russet Burbank unencapsulated and encapsulated tubers.

| Treatments: | Control - minituber alone | 0.96 grams chitin per encapsulated minituber | 0.96 grams chitosan per encapsulated minituber |
|---|---|---|---|
| average number of tubers set | 4.6 b | 5.6 b | 7.6 a |

$P = 0.05$

Table 3 lists combined yield data (number of tubers per plant) at the fifth, sixth and seventh week after the planting of Russet Burbank minitubers. Treated minitubers were encapsulated with 0.96 grams of chitin or chitosan. The data show that significantly greater numbers of tubers at the 99.5 percent confidence level on plants that developed from tubers encapsulated with chitosan as compared to control tubers which were not encapsulated.

TABLE 5

The objective of this study is to test the following hypothesis:

Potato plants germinated from seeds that have been encapsulated in a mixture containing chitin will produce higher levels of chitinase than plants that are not started from chitin encapsulated seeds.

Fungal diseases are a major problem for potato growers, necessitating there use of high levels of pesticides. It is known that chitin can provoke potatoes to release chitinase, which hydrolyzes the cell envelopes of some fungi. In order to expose potatoes to chitin in the filed, a method has been developed to encapsulate the potato seed before planting. The purpose of this study is to determine whether chitinase secretion occurs in encapsulated seeds.

Greenhouse studies were conducted using Russet Burbank potatoes encapsulated in mixtures of six percent chitin or six percent chitosan. Additional seeds were left unencapsulated. Potatoes were placed randomly in a greenhouse and samples were taken every four days for one month. Each sample consisted of at least one-half gram of underground stem which was immediately frozen in liquid nitrogen and stored at −70° C. These samples were then homogenized and assayed radiochemically using tritiated chitin. Preliminary results indicate the presence of chitinase activity in the encapsulated samples, especially those with six percent chitin.

Potato crops require high levels of pesticides, including fungicides. Biological alternatives to toxic chemical fungicides have been sought for many years. Cited from "Cloned chitinases in fungal plant-pathogens control strategies"; written by Oppenheim, Amos and Ilan Chet. The patent application was filed by EnviroGen, Inc., describing seed encapsulation technology as a means of natural fungal control. The application described a procedure in which a mixture containing chitin and other natural materials is used to encapsulate potato seeds before planting.

The reason for using chitin in the packing is to stimulate the growing potato to produce the enzyme chitinase. Chitinase is secreted by plant cells as a natural defense against pathogenic attack. Chitin in the cell wall of fungi is susceptible to being hydrolyzed by chitinase. Cited from "Isolation and characterization of the genes encoding basic and acidic chitinase in *Arabidopsis thaliana*"; *Plant Physiol;* 1990; Vol 93: 907–914. If a potato produces high levels of chitinase, it may be less susceptible to fungal disease. Initial field studies using the chitin encapsulation technology were promising, but they could not give information about the amount of chitinase production in the potatoes. The objective of this study is to establish that elevated levels of chitinase are found in potatoes whose seeds were encapsulated with chitin.

Chitin is a polymer consisting of acetylated $\beta$-1,4-glucosamine. The acetyl group allows chitin to be radioactively labeled using tritiated acetic anhydride. This is the basis for the assaying technique used in this study. When chitin becomes deacetylated, it is known as chitosan. In reality, neither chitin or chitosan exist as purely acetylated or deacetylated polymer. Chitin refers to a mostly acetylated polymer with a few deacetylated saccharides. Chitinase cleaves chitin only next to acetylated groups, producing small chains known as oligomers. FIG. 4 illustrates the action of chitinase on tritiated chitin.

Potatoes were grown in a greenhouse over a 30 day period. Three treatments of potato seeds were planted: 1) seeds encapsulated with six percent chitin, 2) seeds encapsulated with six percent chitosan, and 3) unencapsulated seeds. Five replications of each treatment was prepared one per pot in sterile Metro-mix. Pots were placed randomly in the greenhouse. Samples were taken every three to five days starting at day eleven. At least 0.5 g of underground stem was taken and immediately frozen in liquid nitrogen. Samples were stored at −70° C. until they were assayed.

Radioactive chitin was prepared by swelling 10 g chitosan overnight in 13.4 mL of sodium methoxide and 100 mL methanol at 30° C. After 24 hours, 8.8 mL of tritiated acetic anhydride (25 mCi) was added to the reaction mixture under constant stirring. After another 24 hours at 30° C., the solids were filtered and washed with 750 mL of methanol to remove any free acetic anhydride. The solids were resuspended in methanol and allowed to settle. The small particles that remained in suspension were decanted off to make the radioactive colloidal chitin solution.

The chitinase assay procedure is illustrated in FIG. 5. Crude enzyme extract was prepared by homogenizing stem samples in 5 mL phosphate buffer (pH 6.5). After centrifugation at 15,000 rpm for 10 minutes, 5 mL of the supernatant was transferred to the reaction flask. At time zero, 2 mL of colloidal chitin was also added to the flask and 1 mL reaction mixture was transferred into 1 mL of 1M trichloroacetic acid (TCA). The reaction was allowed to proceed at 37° C. for 30–50 minutes. The reaction was stopped by adding 1 mL of reaction mixture to 1 mL (TCA). For time zero and time final, 1 mL of the TCA/reaction solution was transferred to a microfiltration unit. The filters were then washed with 1 mL TCA and 3 mL of 50 mM phosphate buffer. The filters were then placed in a scintillation vial containing 5 mL of scintillation cocktail. The vials were counted in a scintillation counter to get counts per minute (cpm). All samples were assayed in triplicate.

FIG. 6 illustrates the effect of chitinase on tritiated chitin. As the reaction proceeds, the counts per minute of chitin on the filter decrease. In theory, as chitinase acts on the tritiated chitin it will cleave the polymer chains into smaller oligomers. Unlike the large chains, these oligomers are soluble in water. When the reaction mixture is sent to the microfiltration step, these solubilized oligomers will pass through the filter. Therefore, if chitinase is present the amount of tritiated chitin on the filter should decrease as the reaction proceeds. This graph confirms that our experimental protocol is sound.

FIG. 7 shows the levels of chitinase in underground potato stems over thirty days. Chitase activity is represented by the drop in cpm divided by the reaction time and the mass of stem material originally homogenized, giving cpm/min/g. The activities of the chitosan and chitin encapsulated samples are then divided by the activity of the control for each assaying date. This was done because it was necessary to use several different mixtures of colloidal chitin for the assays, making direct comparison between sampling days difficult. From FIG. 7, it seems reasonable to conclude that the encapsulated seeds produced higher levels of chitinase than the control plants. Chitosan induced some chitinase production, but at lower levels than chitin.

In conclusion, it appears that the initial hypothesis has been satisfied. Potato plants whose seeds were encapsulated with a mixture containing chitin produce higher levels of chitinase than control plants.

We claim:

1. A propagule planting system that controls disease comprising:
   a) a propagule which comprises a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is a stimulus which is not damaging to said propagule, and is provided such that the non-damaging stimulus is at a level:
      i) which sufficiently triggers the release of a naturally defensive substance from said propagule so as to protect said propagule from disease and so that said naturally defensive substance is at a greater level than would naturally exist, and
      ii) which is provided at a level that acts to at least replenish said release of said naturally defensive substance, and
   wherein said non-damaging stimulus is also continuously provided in a non-gaseous form in a vicinity of said propagule;
   c) a non-gaseous communication medium wherein said communication medium allows said non-damaging stimulus to affect said propagule; and
   d) an encapsulant within said vicinity of said propagule which is large enough for said propagule to develop within said encapsulant until said propagule has developed to a point when said propagule is able to withstand disease on its own.

2. A propagule planting system that controls disease comprising:
   a) a propagule which comprises a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule;
   c) a communication medium wherein said communication medium allows said non-damaging stimulus to affect said propagule; and
   d) an encapsulant comprising pentosan within said vicinity of said propagule.

3. A propagule planting system that controls disease comprising:
   a) a propagule which comprises a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule;
   c) a communication medium wherein said communication medium allows said non-damaging stimulus to affect said propagule; and
   d) an encapsulant comprising activated carbon within said vicinity of said propagule.

4. A propagule planting system that controls disease comprising:
   a) a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is continuously provided in a vicinity of said tuber and wherein said non-damaging stimulus causes the release of a naturally defensive substance from said tuber;
   c) a communication medium wherein said communication medium allows said non-damaging stimulus to affect said tuber; and
   d) an encapsulant within said vicinity of said tuber.

5. A propagule planting system that controls disease comprising:
   a) a propagule which comprises a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is continuously provided in a vicinity of said propagule and wherein said non-damaging stimulus causes the release of a naturally defensive substance from said propagule and wherein said naturally defensive substance comprises chitinase, β-1,3 glucanase, protease inhibitors, phenylalanine lyase, chitosanase, PR1 proteins, PR2 proteins, PR3 proteins, PR4 proteins or PR5 proteins; and
   c) a communication medium wherein said communication medium allows said non-damaging stimulus to affect said propagule.

6. A propagule planting system that controls disease comprising:
   a) a pre-germination propagule which comprises a tuber which has an anticipated germination time;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule and wherein said non-damaging stimulus is provided in a manner which does not cause said propagule to germinate, wherein said non-damaging stimulus causes the release of a naturally defensive substance, and wherein said non-damaging stimulus is provided in a manner which coordinates the release of said naturally defensive substance with said anticipated germination time;

c) a communication medium wherein said communication medium allows said non-damaging stimulus to affect said propagule.

7. A propagule planting system that controls disease as described in claim 6 and further comprising an encapsulant within said vicinity of said propagule wherein said encapsulant has a moisture content which is controlled so as to coordinate the release of said naturally defensive substance with said anticipated germination time.

8. A propagule planting system that controls disease comprising:
   a) a pre-germination propagule which comprises a tuber;
   b) a non-damaging stimulus selected from a group consisting of chitin and chitosan and wherein said non-damaging stimulus is provided in the amount of approximately 0.1 grams to 4 grams for each propagule and wherein said non-damaging stimulus is a stimulus which is not damaging to said pre-germination propagule, and is intensely provided in a vicinity of said propagule, such that the non-damaging stimulus is at a level:
      i) which sufficiently triggers the release of a naturally defensive substance from said pre-germination propagule so as to protect said pre-germination propagule from disease and so that said naturally defensive substance is at a greater level than would naturally exist, and
      ii) which is provided at a level that acts to at least replenish said release of said naturally defensive substance, and
   wherein said non-damaging stimulus is provided in a manner which does not cause said propagule to germinate and wherein said stimulus is provided in a non-gaseous form;
   c) a non-gaseous communication medium wherein said communication medium allows said non-damaging stimulus to affect said propagule; and
   d) an encapsulant within said vicinity of said propagule wherein said encapsulant is large enough for said propagule to develop within said encapsulant until said propagule has developed to a point when said propagule is able to withstand disease on its own.

9. A propagule planting system that controls disease as described in claim 1 or 8 wherein said encapsulant further comprises activated carbon.

10. A propagule planting system that controls disease comprising:
    a) a pre-germination propagule which comprises a tuber;
    b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule and wherein said non-damaging stimulus is provided in a manner which does not cause said propagule to germinate;
    c) a communication medium wherein said communication medium allows said non-damaging stimulus to affect said propagule; and
    d) an encapsulant comprising pentosan within said vicinity of said propagule.

11. A propagule planting system that controls disease comprising:
    a) a pre-germination propagule which comprises a tuber;
    b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule and wherein said non-damaging stimulus is provided in a manner which does not cause said propagule to germinate;
    c) a communication medium wherein said communication medium allows said non-damaging stimulus to affect said propagule; and
    d) an encapsulant comprising activated carbon within said vicinity of said propagule.

12. A propagule planting system that controls disease comprising:
    a) a pre-germination tuber;
    b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said tuber, wherein said non-damaging stimulus is provided in a manner which does not cause said tuber to germinate, and wherein said non-damaging stimulus causes the release of a naturally defensive substance from said tuber;
    c) a communication medium wherein said communication medium allows said non-damaging stimulus to affect said tuber; and
    d) an encapsulant within said vicinity of said tuber.

13. A propagule planting system that controls disease as described in claim 12 wherein said tuber comprises a potato tuber.

14. A propagule planting system that controls disease comprising:
    a) a pre-germination propagule which comprises a tuber;
    b) a non-damaging stimulus selected from a group consisting of chitin and chitosan and wherein said non-damaging stimulus is provided in the amount of approximately 0.1 grams to 4 grams for each propagule and wherein said non-damaging stimulus is provided in a vicinity of said propagule, wherein said non-damaging stimulus is provided in a manner which does not cause said propagule to germinate, and wherein said non-damaging stimulus causes the release of a naturally defensive substance from said propagule wherein said naturally defensive substance comprises chitinase, $\beta$-1,3 glucanase, protease inhibitors, phenylalanine lyase, chitosanase, PR1 proteins, PR2 proteins, PR3 proteins, PR4 proteins or PR5 proteins; and
    c) a communication medium wherein said communication medium allows said non-damaging stimulus to affect said propagule.

15. A propagule planting system that controls disease comprising:
    a) a propagule which comprises a tuber;
    b) a non-damaging stimulus selected from a group consisting of chitin and chitosan and wherein said non-damaging stimulus is provided in the amount of approximately 0.1 grams to 4 grams for each propagule and in a vicinity of said propagule; and c) a communication medium wherein said communication medium allows said non-damaging stimulus to affect said propagule.

16. A propagule planting system that controls disease comprising:
   a) a pre-germination propagule which comprises a tuber;
   b) a non-damaging stimulus selected from a group consisting of chitin and chitosan and wherein said non-damaging stimulus is provided in the amount of approximately 0.1 grams to 4 grams for each propagule and in a vicinity of said propagule and wherein said non-damaging stimulus is provided in a manner which does not cause said propagule to germinate; and
   c) a communication medium wherein said communication medium allows said non-damaging stimulus to affect said propagule.

* * * * *